United States Patent
Sanyal

(10) Patent No.: US 9,808,225 B2
(45) Date of Patent: Nov. 7, 2017

(54) RETRIEVAL OF BIOLOGICAL MATERIALS FROM THE HUMAN UTERUS, OVARY AND CERVIX BY SUCTION

(71) Applicant: Mrinal K. Sanyal, Guilford, CT (US)

(72) Inventor: Mrinal K. Sanyal, Guilford, CT (US)

(*) Notice: Subject to any disclaimer, the term of this patent is extended or adjusted under 35 U.S.C. 154(b) by 178 days.

(21) Appl. No.: 14/471,433

(22) Filed: Aug. 28, 2014

(65) Prior Publication Data
US 2015/0065379 A1 Mar. 5, 2015

Related U.S. Application Data

(60) Provisional application No. 61/871,429, filed on Aug. 29, 2013.

(51) Int. Cl.
| | | |
|---|---|---|
| *A61B 10/00* | (2006.01) | |
| *A61B 5/00* | (2006.01) | |
| *B65D 81/00* | (2006.01) | |
| *B65D 33/00* | (2006.01) | |
| *A61F 5/00* | (2006.01) | |

(52) U.S. Cl.
CPC .. *A61B 10/0045* (2013.01); *A61B 2010/0074* (2013.01)

(58) Field of Classification Search
CPC ..... C07K 16/30; A61B 1/303; A61B 10/0045; A61B 2010/0074; A61B 17/42
USPC ....... 600/562, 565, 570, 571, 575, 578, 581, 600/582
See application file for complete search history.

(56) References Cited

U.S. PATENT DOCUMENTS

| | | | | |
|---|---|---|---|---|
| 3,726,277 A | * | 4/1973 | Hirschman | A61F 13/47209 604/359 |
| 3,850,160 A | * | 11/1974 | Denson | A61B 10/02 600/572 |
| 4,182,328 A | * | 1/1980 | Bolduc | A61F 6/225 128/831 |
| 4,280,508 A | * | 7/1981 | Barrada | A61B 10/0048 374/155 |

(Continued)

OTHER PUBLICATIONS

Kinde, et al., "Evaluation of DNA from the Papanicolaou Test to Detect Ovarian and Endometrial Cancers," *Science Translational Medicine*, vol. 5, Issue 167, pp. 1-10, Jan. 2013.

*Primary Examiner* — Rene Towa
*Assistant Examiner* — May Abouelela
(74) *Attorney, Agent, or Firm* — Sunstein Kann Murphy & Timbers, LLP

(57) ABSTRACT

The invention provides devices and methods for self-administered noninvasive retrieval of biological materials of the uterus and/or cervix. The cervical device comprises a receptacle with a variable volume receptacle cavity, a controller configured to change the volume of the receptacle cavity, a surface for collection of biological materials, and a flexible pouch for generation of suction to facilitate efficient retrieval of biological materials. The biological materials retrieved include various biomarkers of diseases and disorders of reproduction, are directly isolated from a site of pathology, and are not metabolized or diluted. Information generated by analyzing these biological materials permits early diagnosis and prognosis assessments of disease and disorders of the female reproductive organs, irregularities of pregnancy, anomalies of the fetus in utero, and microbial infections.

23 Claims, 7 Drawing Sheets

(56) References Cited

U.S. PATENT DOCUMENTS

| | | | | |
|---|---|---|---|---|
| 4,376,634 A * | 3/1983 | Prior | G01N 33/579 | 422/562 |
| 4,467,816 A * | 8/1984 | Schluter | A61B 10/04 | 600/569 |
| 4,628,941 A * | 12/1986 | Kosasky | A61B 10/0291 | 600/572 |
| 4,650,466 A * | 3/1987 | Luther | A61B 17/221 | 604/105 |
| 5,108,927 A * | 4/1992 | Dorn | C12N 1/04 | 435/243 |
| 5,231,992 A * | 8/1993 | Leon | A61B 10/0045 | 128/841 |
| 5,445,164 A * | 8/1995 | Worthen | A61B 10/0045 | 600/572 |
| 5,476,104 A * | 12/1995 | Sheahon | A61B 10/0291 | 600/570 |
| 5,725,481 A * | 3/1998 | Buck | A61B 10/0291 | 600/572 |
| 5,928,184 A * | 7/1999 | Etheredge | A61F 13/2051 | 604/15 |
| 6,039,693 A * | 3/2000 | Seward | A61B 8/06 | 128/916 |
| 6,126,616 A | 10/2000 | Sanyal | | 600/562 |
| 6,475,165 B1 * | 11/2002 | Fournier | A61B 10/0291 | 600/562 |
| 6,702,759 B2 * | 3/2004 | Pevoto | A61B 10/0045 | 600/562 |
| 6,796,973 B1 * | 9/2004 | Contente | A61K 9/0036 | 128/832 |
| 7,207,951 B1 * | 4/2007 | Lurie | A61B 10/0045 | 600/563 |
| 7,333,844 B2 | 2/2008 | Jones et al. | | 600/361 |
| 8,308,652 B2 * | 11/2012 | Rieth | A61B 5/01 | 600/549 |
| 8,460,209 B2 * | 6/2013 | Klein | A61B 10/0045 | 600/569 |
| 8,795,248 B2 * | 8/2014 | Shihata | A61F 5/4553 | 604/327 |
| 9,357,982 B2 * | 6/2016 | Edmunds | A61F 2/005 | |
| 2007/0142746 A1 * | 6/2007 | Scampini | A61B 10/0045 | 600/572 |
| 2011/0021950 A1 * | 1/2011 | Daniels | A61B 10/02 | 600/569 |
| 2012/0199733 A1 * | 8/2012 | Karpas | C12Q 1/04 | 250/282 |
| 2013/0172778 A1 * | 7/2013 | Teschendorf | A61B 10/0291 | 600/569 |

* cited by examiner

RETRIEVAL OF BIOLOGICAL MATERIALS FROM THE HUMAN UTERUS, OVARY AND CERVIX BY SUCTION

CROSS REFERENCE

This application claims priority from U.S. Provisional Application No. 61/871,429 filed Aug. 29, 2013, the contents of which are hereby incorporated by reference in their entirety.

TECHNICAL FIELD

The present invention relates to devices and methods for retrieval of biological materials of the cervix, ovary and uterus for the diagnosis of disease and disorders of the human female reproductive organs, pregnancy and fetal development. The devices and methods of the invention provide for early detection, intervention and prognosis of these diseases and disorders as well as the design of personalized therapeutic protocols for treatment.

BACKGROUND OF THE INVENTION

At present, the procedures for diagnosis of diseases and disorders of the female reproductive system and fetal disorders may involve evaluation by invasive methods, such as, detection of cancer of reproductive organs by colposcopic examination, frequent Pap-smear analysis for cervical, endometrial sampling for endometrial, and endoscopic methods for ovarian cancers and chorionic villous sampling for genomic anomalies of the fetus. These methods of retrieving tissues for the diagnosis of disease and disorders are inconvenient, potentially painful and may pose safety risks. These procedures are expensive and require the participation of health care professionals and facilities. Further, these procedures are invasive with risks of injury to the patient and/or fetus, which can deter frequent monitoring of women for early diagnosis of such diseases and disorders of the reproductive system.

U.S. Pat. No. 7,333,844, the content of which is herein incorporated by reference, is directed to a device for diagnostic measurements such as the pH value of a female patient's uterine tissue. The device includes a catheter with a pH measuring tip inserted through the patient's vaginal canal and into the patient's uterine cavity until the pH measuring active electrode on the distal end of the catheter contacts or penetrates the uterine fundus.

U.S. Pat. No. 6,126,616, the content of which is incorporated herein by reference, teaches a cervical collection device for passive collection of uterine and cervical secretions for medical diagnostic purposes.

There is a need in the art for safe, painless, noninvasive, inexpensive, easy to use devices and methods for retrieval of biological materials for diagnosis of progression of diseases and disorders of the female reproductive system and for monitoring of adverse pregnancy and fetal development.

SUMMARY OF THE INVENTION

The present invention provides novel devices and methods for efficient retrieval and collection of biological materials of the uterus, cervix and ovary of a female subject, wherein retrieval can be performed by the subject, in the absence of a healthcare professional, and wherein the biological materials include but are not limited to cells, secretions, macromolecules, spotted blood and pathogenic microbes. The devices and methods of the invention provide for retrieval and collection of biological materials directly from reproductive organs or from the developing conceptus. The devices and methods of the invention are useful, at least for:

(1) Early diagnosis of cervical, ovarian and endometrial cancers;
(2) Evaluation of genomic anomalies related to fetal birth defects,
(3) Assessment of infertility and improvement in the In Vitro Fertilization (IVF) procedures; and
(4) Detection of microbial infections and sexually transmitted diseases (STD).

The devices and methods of the invention offer numerous advantages over currently accepted procedures including but not limited to: (a) reduced involvement of healthcare professionals for disease and disorder diagnosis, (b) allow for frequent and inexpensive monitoring of multiple diseases and disorders, (c) reduced risk of injuries and discomfort; (d) non-invasive; and (e) increased convenience and cost effective.

In addition, the present invention provides the following advantages over devices and methods for retrieval known in the art: increased viability of biological materials that are collected; simultaneous detection of biomarkers of the cervix, ovary and uterus, collection of concentrated samples of biological material; and detection of DNA and protein biomarkers. Since the device of the invention allows for collection of samples directly from the source of the disease, reduced amounts and unmetabolized biomarkers of a disease or disorder can be quantified as compared to other collection methods and sources (e.g., blood, urine and saliva). The device can be worn by women for prolonged periods (approximately 10 hours), and therefore, large quantities of biological materials can be collected.

In one embodiment, the invention provides for a device for retrieving biological materials of the uterus and/or cervix and/or ovary of a subject comprising: a receptacle having an open end placed over the cervix and a wall defining a variable volume receptacle cavity; and a controller configured to change the volume of the receptacle cavity; the controller having a proximal end and a distal end.

In one embodiment, the device comprises: a removable surface for collection of the biological materials; and a flexible pouch for generation of suction; wherein the surface is removably fitted within the receptacle cavity.

In another embodiment, the device comprises a removable sterile absorption capsule comprising a surface having a platform, wherein the platform comprises permeable materials for collection of the biological materials; a flexible pouch for generation of suction; wherein the capsule is encased for sterility; and is removably fitted within the receptacle cavity following removal of the casing.

In another embodiment the receptacle further comprises a flexible rim extending from the open end and effecting firm attachment of the receptacle over the cervix.

In another embodiment, the receptacle is made of silicone. The silicone can be non-toxic medical grade silicone.

In another embodiment, the surface comprises a platform that has an anterior side and a posterior side, and is oriented such that the anterior side faces the open end of the receptacle and the cervix, and the posterior side faces away from the open end of the receptacle.

In another embodiment, the surface comprises: a pull tab for detaching the surface from the receptacle cavity; and a platform holding a matrix or mesh of permeable substrate materials.

In another embodiment, the platform of the surface comprises: a pull tab for detaching the platform from the receptacle cavity; wherein the platform comprises a matrix or mesh of permeable substrate materials. The matrix or mesh of permeable substrate materials contain solutions for irrigation and washing of the cervical area. The irrigation solution are of different types, such as, physiological saline or tissue culture media fortified with serum proteins, growth factors and hormones, and antibiotics and agents for the preservation of cell viability and integrity of the macromolecules. The irrigation solution incorporates different concentrations of proteolytic (trypsin, pronase and proteinase K), collagenase and DNase or other suitable enzymes alone or in combination to facilitate the release and collection of the biological materials of the cervix surface or endocervical canal and uterine cavity.

In another embodiment, the substrate materials are selected from the group consisting of: cotton mesh, nylon mesh, collagen matrix, hydrogel matrix, synthetic sponge or tissue culture scaffold.

In another embodiment, the pouch is hollow inside and has an anterior wall facing the open end of the receptacle and a posterior wall facing opposite of the open end of the receptacle wall. The pouch can be a suction pouch.

In another embodiment, the pouch is an inflated pouch.

In another embodiment the inflated pouch comprises one or more perforations on the posterior wall.

In another embodiment the controller is configured to expel air contained in the pouch through the perforations of the posterior wall to generate suction.

In another embodiment the pouch is a compressed pouch.

In another embodiment the compressed pouch comprises one or more pillars separating the anterior wall and the posterior wall.

In another embodiment the proximal end comprises a handle and the distal end comprises a bead.

In another embodiment a controller is a string that is at the proximal end of the device and comprises a handle and the distal end comprises a bead.

The invention also provides for a method of retrieving biological materials of the uterus and/or cervix and/or ovary of a subject comprising the steps of: providing a device having a receptacle with an open end and a wall defining a variable volume receptacle cavity and a controller configured to change the volume of the receptacle cavity; positioning the open end of the device facing the cervix of the subject; collecting biological material from the uterus and/or cervix of the subject; and removing the device after a specified time period.

In one embodiment, the method comprises the step of: generating suction by changing the volume of the pouch cavity through the controller.

In another embodiment the method comprises the step of: analyzing the biological material to identify a subject with a particular disease or disorder.

In another embodiment the biological material collected is selected from the group consisting of: uterine cells, cervical cells, glandular secretions, migrating WBCs, migrating RBCs, placental cells, fetal cells, peritoneal fluid of the abdomen, DNA, RNA, antibodies and pathologic microbes.

In another embodiment the disease or disorder is selected from the group consisting of uterine cancer, cervical cancer and ovarian cancer, a disorder of pregnancy, a developmental defect, infertility, and microbial infection.

The invention also provides for a method of detecting a disease or disorder in a first subject, comprising the steps of: providing to the first subject a device having a receptacle with an open end and a wall defining a variable volume receptacle cavity and a controller configured to change the volume of the receptacle cavity; positioning the open end of the device facing the cervix of the first subject; collecting biological material from the uterus and/or cervix and or ovary of the first subject; determining the level of expression of a biomarker indicative of the disease or disorder; wherein an increase or decrease in the level of expression of the biomarker as compared to the level of expression in biological material collected from a control subject that does not have the disease or disorder indicates that the first subject has the disease or disorder.

In one embodiment, the method provides for simultaneous detection of more than one cancer.

In another embodiment, the method provides for early detection of a disease or disorder.

As used herein, early detection refers to detection of a cancer at Stage 0 or Stage 1, for example, as described in the World Wide Web at cancer.gov/cancertopics/factsheet/detection/staging In one embodiment a representative gene(s) or expressed protein/RNA biomarkers are to be identified or quantified in the retrieved biological materials, and these biomarkers are selected from well characterized genes including but not limited to: KRT7, TUBB3, ITGB1, HGF, GH-2, FGF7, HSD3B, CYP19, CGB, ESR1, PAPPA, IGF-1,-2, MMP-2,-9, MUC16, PTEN, CTNNB1, MSH1,-2,-6, TP53, EGFR, FGFR3, ras, myc, HLA-G, DRB, MUC5B, KLK11,13, fFN1, hemoglobin, HBE1 epsilon, α-fetoprotein (AFP), PTEN, MLH1, MSH2, ESR1, PGR, ETV5/ERM, RUNX1/AML1, CYP19, IGF1R, PAX2, CTNNB, PI3K, TP53, p16 [CDKN2A], NFE2L2, HER2/Neu, CLDN1, CD151, MTDH, PTK2, EMP2, EPCAM, IMP3, SSA1, KLK6, VEGF, TGF-β1, CA-125, MUC16, HE-4 (WFDC2), YKL-40 (CHI3L1), IGF1, GDF15 and IL6.

The invention also provides for a method of monitoring the progression of a particular disease comprising the steps of: providing a device having a receptacle with an open end and a wall defining a variable volume receptacle cavity and a controller configured to change the volume of the receptacle cavity; positioning the open end of the device facing the cervix of the subject; collecting biological material from the uterus and/or cervix and/or ovary of the subject at a first time point; removing the device after a specified time period; providing a device having a receptacle with an open end and a wall defining a variable volume receptacle cavity and a controller configured to change the volume of the receptacle cavity; positioning the open end of the device facing the cervix of the subject; collecting biological material from the uterus and/or cervix and/or ovary of the subject at least at a second time point; removing the device after a specified time period, and comparing the biological material collected at the first time point and the biological material collected at the second time point; wherein an increase or decrease in the level of expression of a biomarker in the biological material collected at the first time point as compared to the second time point indicates the progression of the disease.

In one embodiment, the level of expression of a biomarker in the biological material is determined and compared in the biological material collected at the first, second and additional time points.

The invention also provides for a method of designing a treatment protocol for a particular disease comprising the steps of: providing a device having a receptacle with an open end and a wall defining a variable volume receptacle cavity and a controller configured to change the volume of the receptacle cavity; positioning the open end of the device facing the cervix of the subject; collecting biological material from the uterus and/or cervix and/or ovary of an untreated subject at a first time point; removing the device after a specified time period; and analyzing the biological material to determine the treatment protocol for the subject.

In one embodiment the method comprises a step of analyzing the biological material before and after administration of a compound known to treat the disease. The recent innovations in analysis of genomic profiles are used to analyze the biological materials retrieved using the inventive device and allow for identification of the gene(s) involved in a disease and the genomic heterogeneity of such genes, such as, homozygous/heterozygous, copy number variations, germ-line and somatic-mutations, sequence repeats, deletion and insertions and other anomalies of genes and their expression simultaneously. Such identification of different gene anomalies at the base-pair resolution will aid in the precision diagnosis and personalized therapy.

DETAILED DESCRIPTION OF SPECIFIC EMBODIMENTS

Figure 1:
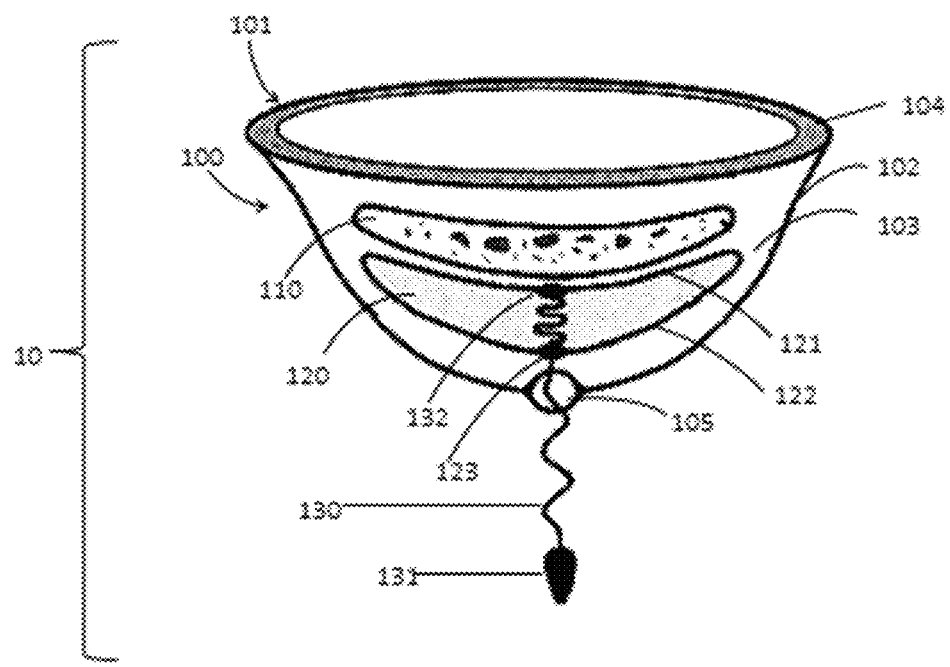
FIG. 1 is a cross sectional view of a device according to the invention, comprising a receptacle for placement over the protruded cervix, a surface having a platform, a pouch for generation of suction, and a controller for self-activation of suction. The device comprises a removable sterile absorption capsule comprising a surface having a platform, wherein the platform comprises permeable materials for collection of the biological materials. The capsule is encased for sterility; and is removably fitted within the receptacle cavity following removal of the casing.

The biological materials associated with cancers of the endometrium and ovary drain into the uterine cavity and pass through the endocervical canal, and can be collected by the uterine device of the invention for diagnosis of endometrial and ovarian cancers. The biological materials of cervical cancer (pre-cancer and cancer cells and human Papilloma virus (cancer causing HPV-16 and -18) are transferred to the absorption capsule as it is in close proximity to the cancer lesions). The device and methods of the invention allows for simultaneous detection of more than one disease, for example, three gynecological cancers described above, or more than one disorder during development or fertility causes or microbial infections. The device for collecting biological materials of this invention and the methods for their analysis allows for early detection of a disease or disorder. The above device for retrieving biological materials of the human uterus and/or cervix, designated generally by numeral 10, is described with reference to FIG. 1. Device 10 comprises a receptacle 100, which has an open end 101 for placement over the protruded cervix, a wall 102 defining a variable volume receptacle cavity 103; a surface 110 for collection of biological materials fitting within receptacle cavity 103 and having a platform; a flexible pouch 120 for generation of suction fitting within receptacle cavity 103; and a controller 130 configured to change the volume of receptacle cavity 103. Controller 130 has a proximal end 131 and a distal end 132.

Receptacle 100 is made of biocompatible materials, such as, non-toxic silicone or synthetic polymers that are at least (1) extremely stable within the environment of the body; (2) durable; (3) reusable; and (4) adjustable in size if needed to accommodate the addition/inclusion of other components of the device. The biocompatible materials comprising receptacle 100 exhibit highly reduced, insignificant or no detectable short-term or long-term systemic and/or local toxic effects on women or the developing fetus. The receptacle and suction pouch can be made of the same material and may be cleaned for repeated use.

Receptacle 100 can be of a hemispheric shape having a diameter between 50 mm to 100 mm, for example, 50 mm, 55 mm, 60 mm, 65 mm, 70 mm, 75 mm, 80 mm, 85 mm, 90 mm, 95 mm and 100 mm, and a depth of from about 20 mm, to about 50 mm, for example, 30 mm. An appropriate size is chosen to fit snugly over the cervix of a subject.

Controller 130 can be a cotton string or may comprise a synthetic material that is non-toxic and non-irritating to the subject of from about 5 cm, to about 30 cm long, for example, about 10 cm long, as desired by the subject. The distal end 132 is firmly attached to anterior wall 121 of pouch 120 when inflated, and is detachable in the compressed pouch. The distal end 131 may comprise a handle, for example, a glass, metal or plastic bead to facilitate its capture. Controller 130 passes through a pouch opening 123 on posterior wall 122 and a receptacle opening 105 on receptacle wall 102. Proximal end 131 hangs freely within the vagina of a subject and is accessible to the subject for self-activation of suction for release of biological materials from the uterus and or cervix.

In a preferred embodiment, receptacle 100 further comprises a flexible rim 104 extending from open end 101 to effect firm attachment of receptacle 100 over the protruded cervix.

Figure 2:
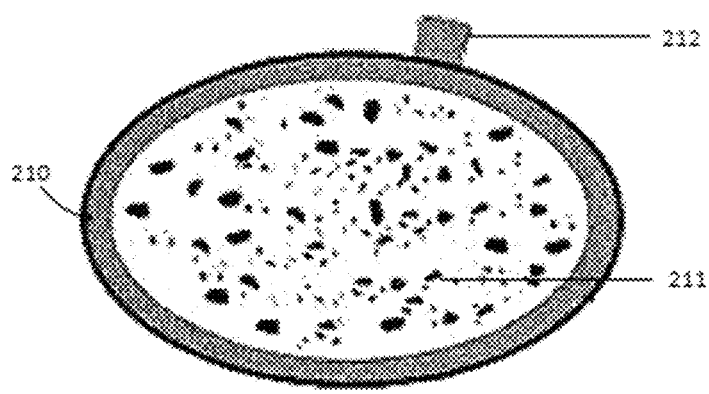
FIG. 2 is a top view of an absorption capsule having a surface with a platform comprising permeable substrate materials with irrigation solution for washing the cervical area and deposition of biological materials from the uterus and/or cervix and/or ovary.

Referring now to FIG. 2, surface 210 holds a platform 211 of the absorption capsule comprising or supporting a matrix or mesh of permeable substrate materials. Different types of substrate components are used for deposition of biological materials released from the uterus and/or cervix and/or ovary. The permeable substrate materials include but are not limited to cotton or nylon mesh, synthetic polymer sponge, collagen or hydrogel matrix, and tissue culture scaffold. The tissue culture scaffolds include but are not limited to sheets or beads of collagen (Cytodex-3) and polyglycolic biopolymer (plain or honeycomb sheets) and permit direct culture of retrieved cells for analysis. These substrate materials can promote and preserve cell viability and integrity of macromolecules from the uterus and/or cervix (for example, DNA, RNA, protein, antibody) that are deposited/retrieved on the platform. These substrate materials may be selectively impregnated with buffered physiological saline or tissue culture media (e.g., DMEM and F10), supplements of sera and growth promoting factors (e.g., β-fibroblast-, insulin like-, hepatocyte growth factors) for irrigation and washing of the cervical area and preservation of the viability of cells for culture and analysis. In addition, fortification of substrates with antibiotics, anticoagulants, and specific enzymes (e.g., trypsin, collagenase, proteinase K, pronase and DNAse) will facilitate the retrieval of biological materials. The components of the substrate, for example collagenase, trypsin, proteinase K, pronase and/or DNAse, can liquefy viscous materials in the cervical canal, for example, the suspension of secretions exuded from glands, exfoliated and migratory cells, fragmented cells and tissues, bacteria and viruses, and cell free macromolecules that are primarily derived from the secretions of female reproductive organs.

In another preferred embodiment, surface 210 further comprises a tab 212 for easy lifting of the surface 210 and for harvesting of biological materials deposited and accumulated on the platform 211 of the surface 210. The platform 211 of the surface 210 can comprise one or more molecules of interest, for example DMEM and F10, supplements of sera and growth promoting factors (e.g., β-fibroblast-, insulin like-, hepatocyte growth factors), antibodies or nucleic acid probes for a marker indicative of a disease or disorder of interest. Such molecules can be provided separately from the surface having a platform. The surface 210 having a platform 211 is sterile and is packaged in the presence of a sufficient amount of solution for irrigation and washing. The components of the solution are suitable for collection and preservation of biological materials appropriate for/indicative of a particular disease or disorder and do not affect the analysis of the diagnostic parameters being analyzed. Following removal of the device, the surface having a platform is detached using tab 212 and the retrieved biological materials are analyzed, for example, for the presence of a biomarker of interest.

Different types of biological materials are deposited and accumulated on platform 211. These biological materials include uterine, ovarian, endometrial and cervical cells (normal, pre-neoplastic or neoplastic cells) and secretions from uterine glands, for example, endometrial glands, migrating white blood cells (WBCs) and red blood cells (RBCs), naturally dislodged placental villous trophoblast cells from the anti-implantation pole and migrating extravillous trophoblast cells and different types of fetal cells, dissolved hormones and factors such as chorionic gonadotropin, pregnancy associated plasma protein, histocompatibility factors, biomarkers of cancers, steroid hormones, peritoneal fluid of the abdomen passing through the fallopian tube into the uterine cavity and cervix, and different types of disease causing and/or harmless microbes. These materials also include biomarker macromolecules (for example, DNA, RNA, protein, antibody) associated with diseases and disorders, fragmented cells and aggregates of fibrin and mucin. These biological materials are derived from the normal and diseased tissues, and because they are not diluted or metabolized, have higher concentrations of cellular or soluble biomarkers, for example indicative of a particular disease, compared to that in systemic sources, such as blood, urine, saliva and others. Therefore, the use of biological materials retrieved by the devices and methods in accordance with the present invention allows early detection and diagnosis of female reproductive diseases and disorders.

Figure 3:
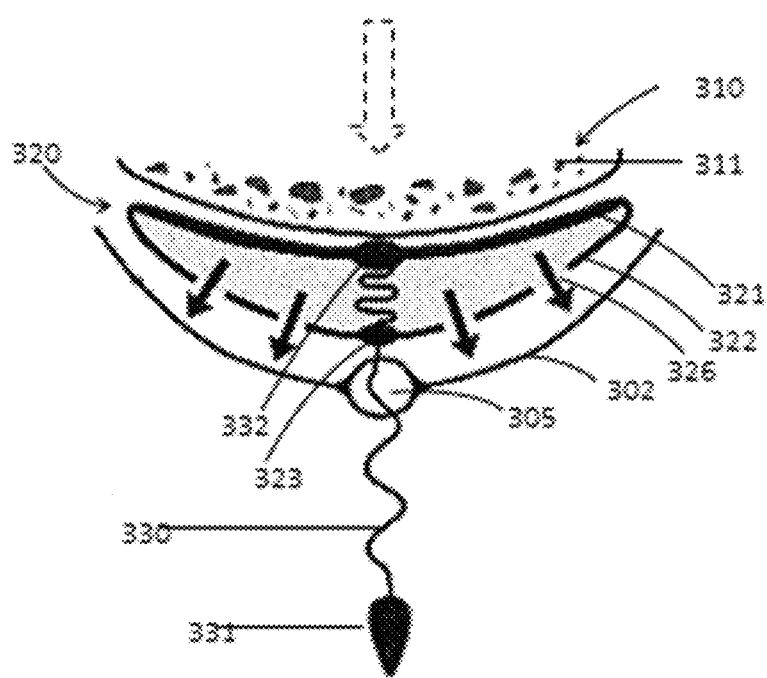
FIG. 3 is a cross sectional view of a device comprising an inflated pouch.

Referring now to FIG. 3, a device comprising an inflated flexible pouch 320 is described. Inflated pouch 320 has an intact anterior wall 321 and a posterior wall 322 having a plurality of perforations 326. Perforations 326 are about 0.25 mm to about 2 mm in diameter, for example, 0.25 mm, 0.5 mm, 1 mm, 1.25 mm, 1.5 mm and 2 mm. Distal end 332 of controller 330 is fixed at anterior wall 321 of pouch 320. Proximal end 331 passes through pouch opening 323 on posterior wall 322 and receptacle opening 305 of receptacle wall 302 into the vagina and is accessible to a subject for pulling of controller 330.

A subject can pull the proximal end 331 of controller 330 to lower anterior wall 321 towards posterior wall 332 to expel the air inside inflated pouch 320 through perforations 326 (depicted by four solid arrows in FIG. 3). Thus, a negative suction pressure (shown as a dashed arrow at the top of FIG. 3) is activated within the uterine cavity to facilitate the release of biological materials. Relaxation of proximal end 331 reverts inflated pouch 320 into its original shape by the influx of air through receptacle opening 305. Repeated pulling and relaxation of proximal end 331 of controller 330 produces suction. The substrate materials in platform 311 also irrigate the cervix area and endocervical canal. The platform is impregnated with irrigation solution which is released during this process for a thorough wash of the cervical area. In addition, enzymes in this solution may liquefy the viscous materials located within the endocervical canal and on the surface of the cervix, thereby, aiding in the extraction of the biological materials.

Figure 4:
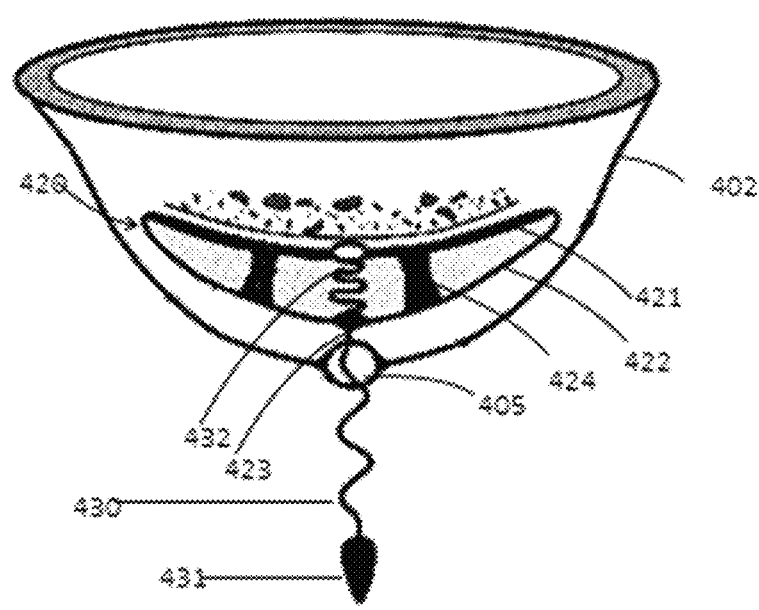
FIG. 4 is a cross sectional view of a device comprising a compressed pouch.

A compressed pouch is depicted in FIG. 4. A compressed pouch 420 has an anterior wall 421 and a posterior wall 422. The anterior wall is stronger than the highly flexible posterior wall, thereby, allowing inflation of the pouch by the influx of air through the perforation on the anterior wall produced by detachment of the controller (string). The rush of air posteriorly facilitates the expulsion of the materials within the endocervical canal and their deposition along with the washing of the cervix on the platform. The walls are separated by a plurality of pillars 424, which are made of elastic materials, for example, non-toxic silicone materials with expansion and compression properties that are adequate to perform the functions required of the compressed pouch. Pillars 424 have a length between 5 mm to 10 mm, for example, 5 mm, 6 mm, 7 mm, 8 mm, 9 mm, and 10 mm, and a diameter of from about 0.5 mm to 1.5 mm, for example, 1 mm. Pillars 424 are in a collapsed position and provide spring-like resistance to separate anterior wall 421 and posterior wall 422.

Distal end 432 of controller 430 is detachably attached to anterior wall 421. Proximal end 431 of controller 430 passes through pouch opening 423 on posterior wall 422 and receptacle opening 405 into the vagina such that the controller 430 is accessible to and can be pulled by a subject.

Figure 5:
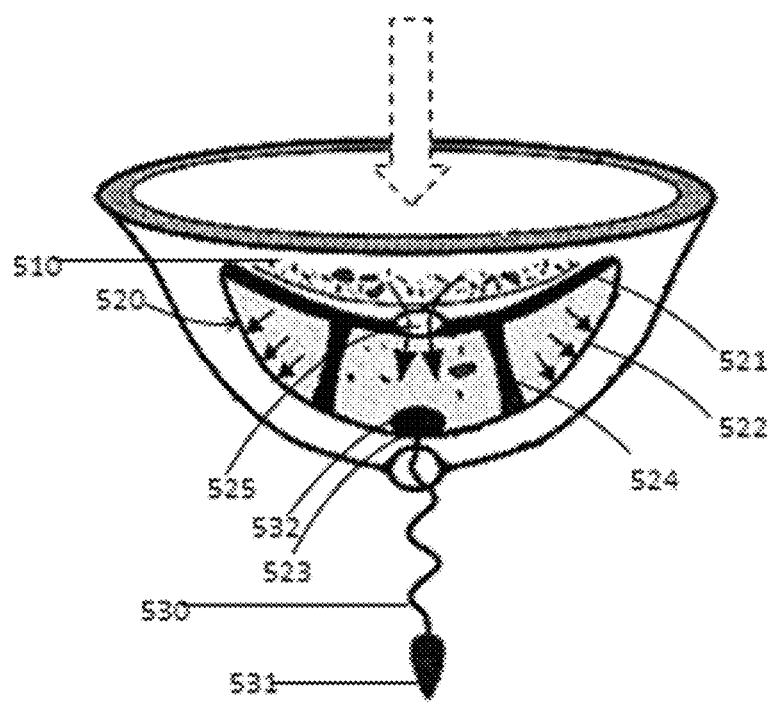
FIG. 5 is a cross sectional view of a compressed pouch activated for generation of suction.
Figure 6:
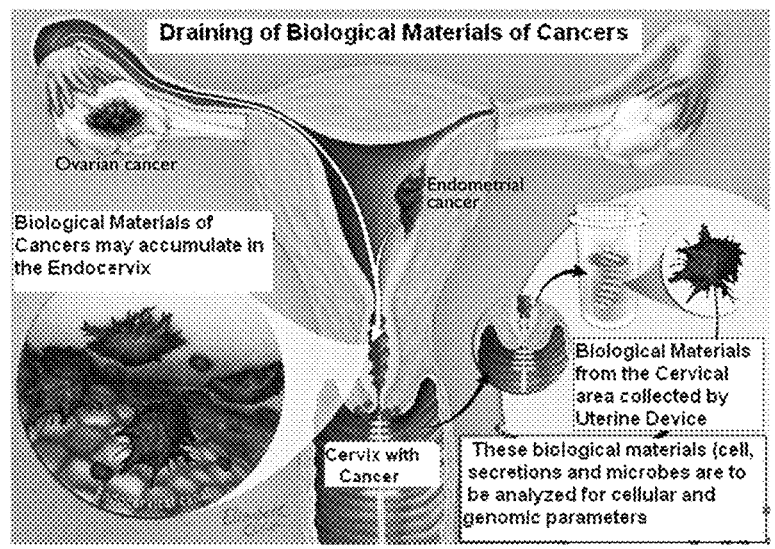
FIG. 6 presents the collection of biological materials of reproductive organ cancers (adapted from Kinde I. et al., Sci Transl Med. 2013 January 9:5 (167):ra4.doi: 10.1126/scitranslmed.3004952).
Figure 7:
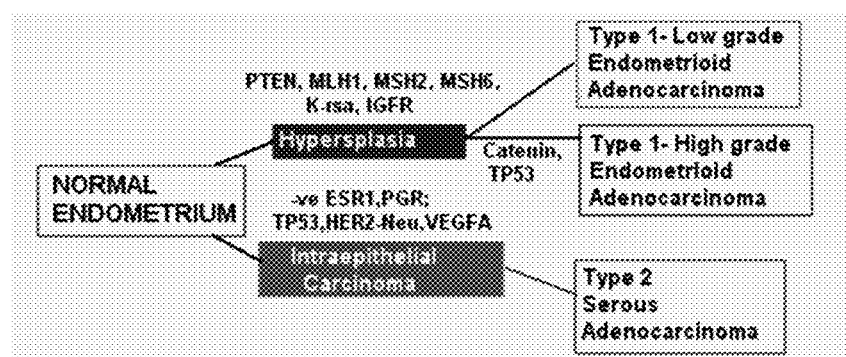
FIG. 7 presents an example of an application of the device: diagnosis of anomalies of genes and their expression features associated with endometrial cancers.
Figure 8A:
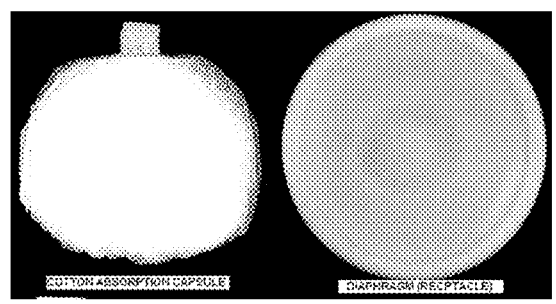
FIGS. 8A-C present the components of the uterine device: absorption capsule and receptacle (A); placement of the device over the cervix marked by number 20 (B); and procedure for the use of the device (C) (U.S. Pat. No. 6,126,616 and literature describing diaphragm provided by Ortho-McNeil Pharmaceuticals).
Figure 8B:
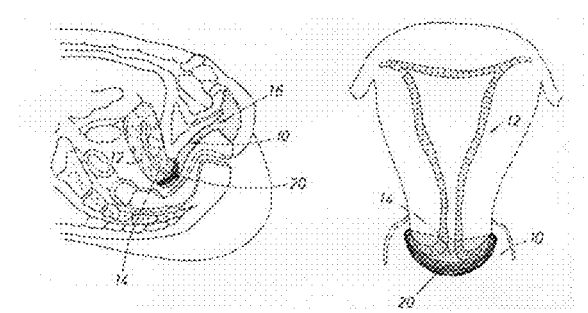
Figure 8C:
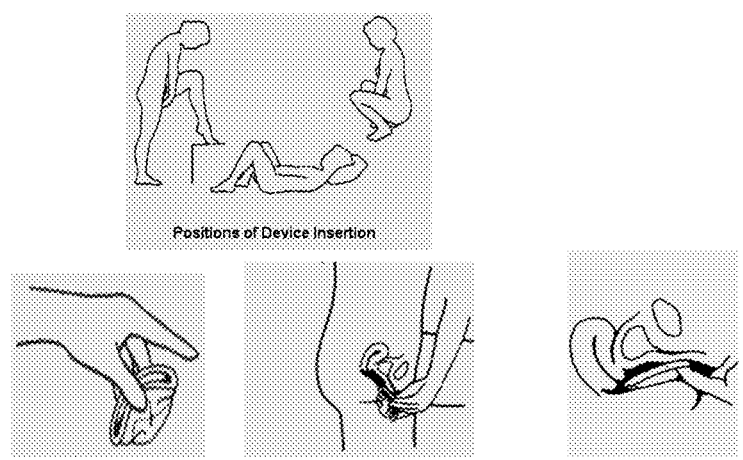

Referring now to FIG. 5, an activated compressed pouch 520 is shown. By pulling proximal end 531 of controller 530, distal end 532 becomes detached from anterior wall 521 and creates a puncture 525 on anterior wall 521. Distal end 532 closes pouch opening 523 on posterior wall 522. Pillars 524 and compressed pouch 520 expand as an influx of uterine air enters the compressed pouch 520 through puncture 525 on anterior wall 521 (shown as several solid arrows in FIG. 5). The influx of air from the uterine cavity (shown as a dashed arrow at the top of FIG. 5) and expansion of compressed pouch 520 generates suction (shown as multiple solid arrows in FIG. 5) facilitates deposition of biological materials over surface 510.

Devices and methods in accordance with the present invention are used to identify diseases and disorders including but not limited to: (i) cancers of the reproductive system (e.g., uterus, ovary and fallopian tube, cervix and specific compartments of these organs); (ii) disorders of pregnancy and developmental defects (e.g., loss of pregnancy, premature labor and fetal genomic anomalies); (iii) infertility conditions; and (iv) various microbial infections, including, sexually transmitted diseases (e.g., chlamydia, gonorrhea and syphilis). Analysis of the biological material retrieved by devices and methods in accordance with the present invention will provide for early diagnosis of diseases and disorders of the female reproductive system, disorders of pregnancy, anomalies of the fetus and microbial infections. The devices and methods of the invention are also used for identification of the appropriate time period for implantation of the embryo in the uterus. Since collection of biological materials using the devices and methods of the invention is convenient and cost effective for subjects, frequent monitoring of women for early detection, prognosis, and intervention of diseases and disorders of women will be possible, and will significantly advance women's health care.

Retrieval of biological samples by devices and methods in accordance with the present invention facilitates diagnosis of diseases and disorders of the female reproductive system. Biological samples can be analyzed by present and new advanced methods known in the art. Macromolecules of biological materials will be amplified by in vitro methods and specific cells separated will be grown in 3-D culture systems. The blood sera of subjects and materials accumulated in the platform are to be quantified for cancer biomarkers by ELISA. The device and methods of the invention allow for analysis of pre-cancer and cancer cells and macromolecules in retrieved biological materials from normal subjects and those with cancers for expression of different genes in cells by simultaneous multispectral cellular immunocytochemistry and anomalies of genes by next generation gene sequencing systems.

Analysis of cells, secretions and microbes collected by the device of the invention for diagnosis of the diseases and disorders include but are not limited to: (i) comprehensive sequencing of genes by the next generation DNA sequencing system and graphic representation of the genomic changes, (ii) simultaneous analysis of multiple biomarker proteins in cell organelles indicating relative expression of the genes, and (iii) 3-D culture of cells identical to normal cells. These methods of analyzing genes and simultaneous characterization of multiple parameters in cells will assist early diagnosis of women's reproductive diseases and fetal disorders and their management.

The pre-cancer and cancer cells are be evaluated by simultaneous immunocytological analysis of reduced expression of multiple cell parameters using a multispectral optical system, and anomalies of cancer related genes by next-generation gene sequencing systems. Comprehensive analyses of gene expression in cells and the anomalies in genes (mutations, gene copy numbers, deletions or addition of bases) and their graphic representation in retrieved samples and that of normal (GenBank database) may show the genomic changes associated with different types of cancers. Molecular information generated in biological materials collected by the noninvasive self-collection procedure of the invention using a uterine device and advances of diagnosis parameters, allows for precision diagnosis, prognosis and risk assessment, intervention and personalized therapy of such cancers.

Magnetic cell sorting for isolation of cells by metallic beads coated with specific antibodies permits separation of different cell types. Cells expressing a particular surface antigen adhere to metallic beads coated with antibody and are separated by a magnetic probe. In addition, laser tweezers allow isolation of a small group of cells by an optically clear polymer capture film for cytological analysis. The biological samples collected using the devices and methods of the invention are analyzed for the presence of biomarkers by methods well known in the art, for example, analysis of cellular parameters by multispectral immunocytochemistry, quantitative PCR and microanalysis of nucleic acids, and microarray and ELISA analysis of protein biomarkers. The components of the biological samples can be separated, for example, cells and or microbes, by centrifugation, and soluble products and their constituents identified by different chromatography methods. The cell free macromolecules, biological secretions or those macromolecules isolated from cells can be assessed by microarray analysis, PCR or next generation gene sequencing systems for sequence variations or mutations, the presence or absence of a gene of interest and, in particular, identification of sequence variations that are specific to disease and disorders of interest.

The cells and fluids of the biological materials retrieved may be assessed for the presence or absence of genes and gene functions associated with different cell properties, diseases and/or disorders, including but not limited to genes and gene products relating to cell structure (KRT7, 20; TUBB3, ITGB1), growth factors (HGF, GH-2, FGF7), those related to pregnancy and trophoblast functions (HSD3B, CYP19, CGB; ESR1, PAPPA, IGF-1,-2, MMP-2,-9), and cancer processes (MUC16, PTEN, CTNNB1, MSH1,-2,-6, TP53, EGFR, FGFR3, ras, myc), and cervical cancer specific Human Papilloma Virus, HPV-16 and -18. Information on the potential for embryo implantation (histocompatibility antigens, HLA-G,-DRB), uterine function (MUC5B; KLK11,13), and fetus specific proteins (fibronectins, fFN1; hemoglobin, HBE1 epsilon 1) for preterm birth, and $\alpha$-fetoprotein (AFP) for fetal neural anomalies, can be generated using such biological materials. Similarly, protein biomarkers and sequences of genes may be used to diagnose various microbial infections. Detailed information on these genes is available in different data bases and the World Wide Web, for example at the websites: ncbi.ninnih.gov and ncbi.nlm-.nih.gov/omimi.

Representative genes associated with hyperplasia and endometrioid cancers are, cell division factor (PTEN), DNA mismatch repair proteins (MLH1, MSH2), estrogen and progesterone receptors (ESR1, PGR), transcription factors (ETV5/ERM; RUNX1/AML1) and diverse genes (e.g., CYP19, IGF1R, PAX2, CTNNB, PI3K). While the genes associated with more aggressive papillary and serous uterine carcinoma are, Nuclear factors (TP53, p16 [CDKN2A], NFE2L2), EGF receptor (HER2/Neu), Claudins (CLDN1), Tetraspanins (CD151), astrocyte elevated gene1 (MTDH), Focal Adhesion Kinases (PTK2, EMP2), epithelial cell adhesion molecule (EPCAM), nucleolar ribonucleoprotein (IMP3), amyloid A (SSA1), Kallikrein 6 (KLK6), vascular endothelial factors (VEGF) and transforming growth factor (TGF-$\beta$1). Microarray analysis indicated differential expression of genes which may diagnose uterine cancers and predict prognosis. The levels of biomarker factors: CA-125 (MUC16), HE-4 (WFDC2), YKL-40 (CHI3L1), insulin like growth factor-1 (IGF1), differentiation factor-15 (GDF15)

and interleukin-6 (IL6) in patient sera are used to assess uterine cancers. Similar protein and genomic characterization will be possible for ovarian and cervical cancers.

Such biospecimens of gynecological cancers that are harvested facilitate research on the origin and progression of such cancers, the role of the micro-environment and determinants of invasion, the interactions of different genes influencing transformation and invasion, and the synergistic effect of regulatory factors, gene mutations and epigenetic mechanism on such cancers. The relationships of germ line mutations causing uterine cancer to other cancers (e.g., uterine cancer and Lynch syndrome), predisposition, impacts of gene mutations and epimutations on such cancers, and processes related to bleeding and uterine cancers are explored. Isolation of specific cell types and their 3-D culture, simultaneous multispectral analysis of different cell parameters, and application of next-generation DNA sequencing systems for more accurate sequencing of genes identifying sequence anomalies, are transformative technologies and far superior to those currently used.

The cells retrieved by devices and methods in accordance with the present invention can be cultured for chromosomal analysis and macromolecules of interest can be isolated from these cells and characterized. DNA, RNA and/or protein isolated from the cultured cells and/or retrieved in the absence of cells using the methods of the invention can be used for prenatal diagnosis of genomic diseases. Numerous diseases associated with genetic abnormalities, such as, Thalassemia, Cystic Fibrosis, Tay-Sachs disease, Muscular Dystrophies, etc., can be identified with cellular and cell-free DNA and/or RNA dissolved in the fluids retrieved using the devices and methods of the invention. Microarrays of single nucleotide polymorphism loci of different genes or next generation sequencing systems may identify specific changes in the genes of the biological samples collected using the devices and methods of the invention. Gene profiles related to a particular disease for screening may be generated using DNA or RNA isolated using the inventive devices and methods.

The biological materials collected according to the methods of the invention can be analyzed simultaneously for biomarkers useful for detection of multiple diseases/disorders of women, pregnancy and fetal disorders and microbial infections. The substrate materials of the inventive device can comprise specific antibodies or nucleic acid probes for biomarkers of interest for isolation and culture of different cell types. Such methods of analysis of biomarkers of diseases and disorders and microbes obtained directly from the source tissue or organ in an undiluted form and in the absence of manipulation, will permit early diagnosis of a pathology or identification of a pre-disease state and therefore allow for early intervention and amelioration of a disease or disorder.

Cells retrieved from the absorption capsule platform are to be assessed routinely by immunocytochemistry of multiple biomarkers for early diagnosis of cancers. Since the neoplastic cells may not be available in sufficient quantities, the neoplastic cell will be purified and cultured by a 3-D culture system resembling the in vivo environment. Diverse anomalies of the genes associated with different types of gynecological cancers are now characterized using next generation sequencing systems that permit parallel rapid sequencing of DNA for precise elucidation of genomic alterations related to cancers.

Medical grade silicone will be used for the production of receptacle and suction pouches of the Uterine Device. Silicone with appropriate physical properties and no toxic effects is used for human applications. Silicone useful according to the invention includes NuSil2, which is currently used for numerous medical devices (see the world wide web at nusil.com/products/healthcare/index.aspx). Various other silicones will be tested for efficiencies for adherence to the cervical protuberance, durability and cleaning, and most importantly suction generation by the elastic properties of silicone used. The use of Silastic Biomedical Grade Liquid Silicone elastomers manufactured and tested by Dow Corning (see the world wide web at dowcorning.com/content/discover/discovershowcase/healthcare.aspx; that exhibit reduced toxicity exceeding the acceptance criteria of 30 day contact duration tests for cytotoxicity, irritation, sensitization, genotoxicity, hemocompatibility, and systemic acute toxicity are to be used.

A platform of the absorption capsule with permeable mesh and a solution suitable for irrigation and wash of the cervical area is used (absorption capsule). A matrix of fibers (cotton or nylon mesh) will be layered over a membrane platform. The cotton/mesh will be impregnated with culture media containing anticoagulants, enzymes and antibiotics for irrigation and thorough washing of the cervical area. Other useful substrates are collagen sheet and bead (Cytodex-3), hydrogel and different types of polymer scaffolds (culisphere, honeycomb and ployglycolic matrix). The irrigation solution may also contain reduced concentrations of one or more non-toxic natural human enzymes (trypsin, collagenase, proteinase K, pronase and DNAse) for softening and/or liquifying viscous materials. Some of these enzymes are used in humans for therapy. However, they could be a concern at high concentration, a low concentrations are to be used in sufficient intervals for healing of the tissues. These tissues are highly resistant to toxicity as spermicidal Nanoxinol-9 are routinely used without know deleterious effects. Remedial treatment may be use of excess substrates, pH alteration, enzyme inhibitors and chelating agents in tampons may be instituted if required. In addition, different growth factors (e.g., IGFs) and sera are incorporated for preservation of cell viability and macromolecular integrity. Absorption capsules of different types, encased for sterility, are designed based on the disease and diagnosis parameter to be assessed. The absorption capsule is encased for sterility, for example, in packaging used for encasing, a disposable bandage or alcohol swab.

Current health care applications of devices and methods of the present invention include, but are not limited to the following:

Assessment of Infertility and Uterine Function:

The uterus is a vital accessory reproductive organ in women involved in menstruation, implantation of embryo, and support of pregnancy. The uterus is a hollow vessel with an inner glandular lining and external muscular tissues. Among the numerous effects of ovarian hormones (estrogen and progesterone), enlargement of the uterine glands and production of secretions, reflect the functional status of the uterus. Anomalies in remodeling of uterine cells and cyclic changes are indicators of infertility which can be assessed by the presence or absence of biomarkers in cells and glandular secretions. The cells and glandular secretions retrieved by the devices of the invention, therefore, aid in the diagnosis of fertility disorders as they indicate the functional status of the ovary, the occurrence of ovulation, embryo development and pregnancy. The potential for implantation of an embryo and pregnancy initiation can be identified by the uterine cells and secretions produced and collected by the inventive device. Uterine priming and the appropriate window of time for transfer of embryos into the uterus during the in vitro fertilization procedure can be more accurately determined by analysis of cells and secretions retrieved by the inventive devices. The outcome of fertility treatments can be improved significantly by cytological and genomic analysis of the cells and secretions collected by the device of this disclosure.

Evaluation of Pregnancy and Fetal Development:

As the embryo implants into the uterus, the trophoblast cells from the developing placenta are dislodged from the anti-implantation pole of the embryo during early human pregnancy (first trimester). Such shedding of trophoblast cells is a normal process. These trophoblast cells available in the uterine cavity, however, have numerous biomarkers of pregnancy and genomic materials for analysis of birth defects earlier in gestation as compared to that possible with other available body fluids (blood, urine and saliva) or biopsied trophoblast tissues. The level of biomarkers of pregnancy (e.g., CGB, PAPP-A, IGFs, MMP-2,-9), fetal hemoglobin, alpha-fetoprotein and fibronectin in the uterine fluids, and genomic changes in the cells retrieved by the devices of the invention may identify the risk of pregnancy loss, intra uterine fetal growth retardation, preterm birth and fetal neural anomalies. The methods for detection of birth defects using dislodged trophoblasts, DNA, RNA, protein and/or antibodies collected by devices and methods in accordance with the present invention are radically different from methods that are presently used, for example, involving highly invasive chorionic villous sampling for biopsy of chorionic villous tissues for diagnosis of birth defects in the fetus due to chromosome anomalies (e.g., Down Syndrome) and gene mutation (e.g., Muscular Dystrophy, Tay Sachs disease). Application of superior cytological methods for reduced cell expression and next generation gene sequencing of the biological materials collected by the devices of the invention allow for significant progress in this area.

Detection of Uterine, Ovarian, and Cervical Cancers:

Different methods well known in the art are used for clinical diagnosis of such cancers, including endoscopic and ultrasound visualization and biopsy for ovarian and endometrial cancers and Pap-smear analysis for cervical cancers. These methods require a subject to be seen by a health care professional. The biological materials retrieved by devices and methods in accordance with the present invention, can be analyzed by ELISA for protein biomarkers, such as, CA-125 (MUC16), HE-4 (VVFDC2), YKL-40 (CHI3L1), IGFs and interleukin-6 (IL6). Analysis of the biological materials using microarrays of expression of different macromolecules and sequence variants of genes specific to such cancers, will markedly improve the diagnosis and prognosis assessment of cancers of female reproductive organs. Since the devices and methods in accordance with the present invention are inexpensive and easy to use by the subject, and require reduced participation of healthcare professionals and healthcare facilities, monitoring of women and early detection of such cancers will be possible. Early detection of uterine, ovarian and cervical cancers will save lives by allowing for immediate intervention and the design and development of personalized treatment protocols.

Relevant data base for markers associated with cancers include but are not limited to: The National Center for Biotechnology Information (NCBI: GenBank, dbSNP, Unigen, etc.), Catalogue of Somatic Mutations (COSMIC) and The Cancer Genome Atlas (TCGA), Online Mendelian Inheritance in Man (OMIM).

Early Diagnosis and Improvement in Diagnosis Procedures

Staging systems for cancer have evolved over time. They continue to change as scientists learn more about cancer. Some staging systems cover many types of cancer; others focus on a particular type. The common elements considered in most staging systems are as follows:

Site of the primary tumor and the cell type (e.g., adenocarcinoma, squamous cell carcinoma)

Tumor size and/or extent (reach)

Regional lymph node involvement (the spread of cancer to nearby lymph nodes)

Number of tumors (the primary tumor and the presence of metastatic tumors, or metastases)

Tumor grade* (how closely the cancer cells and tissue resemble normal cells and tissue The TNM system is one of the most widely used cancer staging systems. This system has been accepted by the Union for International Cancer Control (UICC) and the American Joint Committee on Cancer (AJCC). Most medical facilities use the TNM system as their main method for cancer reporting.

The TNM system is based on the size and/or extent (reach) of the primary tumor (T), the amount of spread to nearby lymph nodes (N), and the presence of metastasis (M) or secondary tumors formed by the spread of cancer cells to other parts of the body. A number is added to each letter to indicate the size and/or extent of the primary tumor and the degree of cancer spread.

Primary Tumor (T)

TX: Primary tumor cannot be evaluated

T0: No evidence of primary tumor

Tis: Carcinoma in situ (CIS; abnormal cells are present but have not spread to neighboring tissue; although not cancer, CIS may become cancer and is sometimes called preinvasive cancer)

T1, T2, T3, T4: Size and/or extent of the primary tumor

Regional Lymph Nodes (N)

NX: Regional lymph nodes cannot be evaluated

N0: No regional lymph node involvement

N1, N2, N3: Degree of regional lymph node involvement (number and location of lymph nodes)

Distant Metastasis (M)

MX: Distant metastasis cannot be evaluated

M0: No distant metastasis

M1: Distant metastasis is present

For many cancers, TNM combinations correspond to one of five stages. Criteria for stages differ for different types of cancer.

| Stage | Definition |
| --- | --- |
| Stage 0 | Carcinoma in situ |
| Stage I, Stage II, and Stage III | Higher numbers indicate more extensive disease: Larger tumor size and/or spread of the cancer beyond the organ in which it first developed to nearby lymph nodes and/or tissues or organs adjacent to the location of the primary tumor |
| Stage IV | The cancer has spread to distant tissues or organs |

Frequent Monitoring:

At present, the procedures for diagnosis of diseases of women, disorders of the fetus, and assessment of post-natal susceptibility to diseases are neither convenient nor efficient.

Early diagnosis of numerous diseases is possible by identifying genomic changes and expression of different macromolecular parameters in cells. The methods of the invention provide for early diagnosis of a disease or disorder by frequent monitoring and assessment of the expression profiles of different cell and organelle parameters or markers. The methods of the invention provide for early detection of: (i) cancers of the reproductive organs, (ii) birth defects of the unborn baby, (iii) infertility and inability to conceive, and (iv) microbial infections and STDs. The device of the invention is inexpensive and easy to use by a subject thereby making possible frequent monitoring for early detection of the diseases and fetal disorders be possible. Collection of biological materials with the device of the invention is painless and noninvasive. In addition, the device allows self-collection that requires no or minimal involvement of a healthcare professional and facilities. Frequent monitoring for diseases and disorders will result in marked improvement in women's health care.

Molecular Methods for Diagnosis:

The parameters of diagnosis of women's diseases and fetal disorders, currently used, have many limitations. For precision diagnosis, next generation gene sequencing systems for generation of in-depth information on genes of cells and secretion recovered are used. The cells retrieved will be analyzed by multispectral immunocytological methods revealing reduced or increased expression or occurrence of different macromolecular parameters in cells and/or organelles and in different cellular compartments including membranes, mitochondria, Golgi body and endoplasmic reticulum. Such data on the alteration of a gene and expression of a gene product allows for precise diagnosis of diseases and assessment of disease prognosis. The analytical methods provide more reliable medical information earlier, enabling the medical professional and the patient to act more proactively.

Diseases and Disorders

Cancers of the Cervix, Uterus and Ovary

Sample Collection for Cervical, Uterine and Ovarian Cancer Analysis: The device of the invention provides for retrieval of biological materials of cervical, ovarian and uterine cancers and their analysis by both cellular and molecular methods for early identification of cancer. Exfoliated cells, secretions, HPV for cervical cancer, and neoplastic cells expressing marker antigens in the vaginal blood and secretions exuded for endometrial cancer, and biomarkers for ovarian cancers are analyzed in-depth for early diagnosis. Early diagnosis may prevent cervical surgeries, expensive hysterectomies and ovary and fallopian tube removal which will extend survival of the patient. At present, women are monitored for cervical cancer by cancer cells in the Pap smear and HPVs, the causal factor for cervical cancer in women, as their persistent presence indicates the risk of cervical cancer. Routine monitoring of cervical cancer and HPVs is possible with the device of the invention and the cost of this monitoring is be highly reduced compared to current costs. These method will be more useful in areas with sparse medical care, and an important step toward cost reduction for women's health care cost as cervical cancer screening is widely performed and the process is expensive. Similarly, for different sub-types of uterine cancers diagnosis by biomarkers in the retrieved biological materials will provide marked health benefit, especially to perimenopausal and menopausal women. Finally, there are no obvious symptoms for early detection of ovarian cancers which mostly originate from the fallopian tube and spreads to ovarian tissues and abdomen. At present, ovarian cancers are diagnosed at late stages. Therefore, early detection of ovarian cancer by the uterine cavity materials and now by the device of the invention are a major advance in gynecological cancer care. The uterine fluids trickle through the endocervical canal which can be collected by the uterine Device disclosed in this application.

Fetal Birth Defects

Birth defects are a leading cause of infant death in the United States. Different types of structural and functional birth defects may originate in utero during pregnancy and can be identified by ultrasonographic imaging and postnatal physical screening. The impact of developmental anomalies is often serious on the surviving children. They may reduce the quality of life of the individual as an adult, and the social cost for the care of the disabled children is also high. The most prevalent disorders of prenatal development are prematurity and intrauterine growth retardation (IUGR) caused by genomic factors and exposure to environmental agents. Dysmorphogenesis of vital organs of the body (e.g., heart structures, skeletal deformities, and anomalies of the eyes, neural tube defects and errors in development of brain and reproductive organs), are, to a great extent regulated by multiple genes. A vast majority of birth defects are associated with anomalies of chromosomes (e.g., Down syndrome). Diseases due to alteration of single genes (e.g., multiple sclerosis, Tay-Sachs, Muscular dystrophy, etc.) inherited from the parents also have significant impacts on developing children and as an adult.

At present, these diseases are diagnosed during in utero development by CVS (Chorionic Villous Sampling) which is a painful and risky procedure. The method of the invention provides for collection of biological materials that can be subject to genomic analysis, wherein the biological materials comprise at least trophoblast cells (genetically equal to that of fetus) are dislodged extensively from the anti-implantation pole which is a natural process, migratory extravillous trophoblast, and fetal cells. In addition, nucleic acids of disintegrated dislodged trophoblast cells and other cellular materials available in collected biological materials exuded from the uterus are used for such analysis. These cells and macromolecules released from the uterine cavity are collected using the device of the invention. The cells and macromolecules retrieved by the device can be of the invention are analyzed in-depth by both cellular and genomic procedures for precision diagnosis of such hereditary diseases.

Neural Anomalies:

Among the various neural anomalies, dysmorphogenesis associated with the differentiation and closure of neural tube, neural crest and mesoderm are most common. They are highly disabling to an individual's growth and functioning. Severe cases of dysmorphogenesis of the neural tube and cephalic development are fatal. Differentiation of primordial neural tissues is regulated by multiple genes promoting multiplication, differentiation and morphogenesis, and dysfunctions of such genes result in diverse structural and functional anomalies of the neural tube and brain. Application of new methods of analysis by multispectral cell analysis and next generation sequencing systems may allow prediction of such defects earlier and more precisely.

Disorders of the Cardiovascular System:

Congenital heart defects affect 1-2% of new born children. It is a leading cause of death in infants under one year of age and represents approximately 25% of all congenital anomalies. Genomic studies have suggested that multiple genes may be associated with such heart disorders. Characterization of genes associated with heart development and anomalies with next generation gene sequencing system will greatly enhance its early diagnosis.

Biological Material Collection for Birth Defects Analysis:

At present, birth defects diagnosis involves invasive CVS soon after pregnancy confirmation ($8$-$9^{th}$ of gestation) to obtain placental trophoblastic tissues which contain the genetic material identical to that of the fetus. These placental tissues are analyzed for chromosome composition and other genomic anomalies for diagnosis of birth defects in the fetus growing in utero. According to the methods of the invention, dislodged placental trophoblast and fetal cells, and DNA available in the uterine effluents, are collected by the device of the invention for diagnosis of such birth defects. The trophoblast cells at the anti-implantation pole are dislodged during early stages of pregnancy. These dislodged placental cells from the anti-implantation pole, as well as migrating fetal and extravillous trophoblast cells, and macromolecules (DNA) in uterine effluents allow diagnosis of birth defects associated with genome anomalies. These placental and fetal cells, isolated by using magnetic cell sorting (MACS), can be used for diagnosis of fetal genomic disorders. Anomalies of different genes (mutations and SNPs) of genes associated with the fetal disorders will be identified by recent innovations of DNA analysis Infertility and Window of Embryo Transfer for IVF Procedure:

Uterine tissues undergo changes during the different phases (follicular, luteal and bleeding) of the menstrual cycle.

The uterine glands are differentiated during the secretory phase. These changes are induced by cyclic secretion of pituitary gonadotrophins and generation of steroid hormones (estrogen and progesterone) from the ovaries. In addition, different growth and regulatory factors, LIF, VEGF, TGF-$\beta$, Leptin, activin, prolactin, corin, Kisspeptins, galectin 3, IGFs and IGF-binding proteins and receptors of these factors, as well as steroidal hormones play a significant role in the preparation of endometrial tissues for implantation of the embryo. The endometrial glands secrete abundantly, in particular, during the secretory phase. The hormonal biomarkers, cytokines profiles and proteins secreted by the endometrial and decidual tissues can be assessed by the biological materials collected.

A large number of fertilized embryos are normally lost during early development (1 viable out of 10). It is estimated that 30% of fertilized embryos lead to successful pregnancy and normal progeny. Approximately 60% of embryos are lost by the second week and 10% during the $3^{rd}$ and $6^{th}$ week of gestation, and late abortion and major malformation claims 3-4%. The factors for such unsuccessful pregnancies are: inadequate preparation of the endometrium, the absence of immunocompatibility, and embryo anomalies. These processes may also play important roles in the failure of the IVF procedures.

In the IVF procedure, mature oocytes are retrieved from the ovary of women treated with gonadotrophins, they are then fertilized by sperm in vitro, and grown into morula of multiple blastomeres (cells), and finally into a hollow ball of cells, blastocysts. Such embryos are then transferred to the receptive uterus for implantation, pregnancy and further growth and development. The invention provides for identification of markers for assessment of maturity of the endometrium and the most appropriate time (window) for embryo implantation using cells and secretion collected by the device of the invention.

Sample Collection for Infertility and Window for IVF Embryo Transfer:

The human endometrium of uterus exhibit cyclic changes correlating with the systemic hormonal changes. The device of the invention collects secretions generated by the endometrium and decidua, the composition of these secretions reflecting the activities of different tissues of the uterus. Exfoliated cells and lymphocytes populating the uterine cavity are analyzed. The methods of the invention allow for in-depth characterization of the biomarkers in the effluents and cells collected by the device during different phases of the menstrual cycle. Identification of such biomarkers aids diagnosis of infertility conditions and an assessment of the receptiveness of the endometrium related to the loss of embryo and failure of implantation. The methods allow for determination of specific uterine conditions that promote infertility and optimal uterine priming for embryo transfer into the uterus for implantation in the IVF-procedure.

Detection of Infection and Sexually Transmitted Diseases:

More than 65 million individuals in the U.S. currently live with sexually transmitted diseases (STD), and approximately 19 million new infections will occur each year. Bacterial STDs (e.g., gonorrhea, chlamydia, and syphilis) are more common than viral STDs (genital herpes, genital warts, hepatitis and HIV). The biological materials collected in the absorption capsule of the device are rich in different microbial population. These microbes are cultured for identification of specific STDs and possible deleterious effects of STDs. The recent CDC guidelines for treatment of different STDs include an expansion of diagnostic evaluation procedures and application of new molecular diagnostic methods. The use of the device and molecular methods of the invention enhances surveillance and monitoring for prevention and therapy of microbial infections. There is an urgent need in this regard as some types of STD microbes are becoming drug resistant. In addition, increased STD infection among the adolescent population is a national and international concern.

Sample Collection for Detection of Microbes:

Routine monitoring of the bacteria and viruses in the uterus and cervix is possible with the use of the device. These microbes are collected by the device in complete privacy. The methods provide for analysis of at least chlamydia, congenital syphilis and gonorrhea. Following collection, the capsules of the device are extracted for analysis of diverse microbes by current and new procedures.

Identification of Bacterial and Viral Infection Analysis:

The biological materials retrieved by devices and methods in accordance with the present invention contain diverse bacterial and viral populations, including those associated with sexually transmitted diseases (Chlamydia, gonorrhea and syphilis) and pathological viruses (Human Papilloma, Cytomegalovirus and HIV). These may be identified directly or after culture. The devices and methods in accordance with the present invention are an important tool for reducing/preventing the occurrence of sexually transmitted diseases that can be used in private by a subject. The use of devices and methods in accordance with the present invention will radically improve the control and management of such diseases.

Monitoring of Disease Progression:

By retrieving biological samples using the devices and methods of the invention at different time points, the progression of a disease or disorder, or the progression of a pregnancy can be monitored. This will facilitate treatment of a disease as well as maintenance of a pregnancy.

Design of a Therapeutic Protocol:

A therapeutic regime for treating a particular cancer or disorder can be determined by retrieving biological samples from a subject in need using the devices of the invention and analyzing the samples for the presence or absence of a biomarker indicative of the disease or disorder. Depending on the level of a particular biomarker, a particular therapeutic protocol is used. A biological sample can also be assessed for an indicia of a negative side effect of a particular treatment to determine if a therapy should be discontinued. Personalized therapy protocols for the treatment of cancers of the female reproductive organs may be designed in accordance with genomic changes and or changes in the expression pattern of a biomarker. Genomic changes associated with fetal development are not only indicative of the potential for disease, but are also indicative of susceptibility to future diseases and potential life-style risks in post-natal life as a child or adult.

Parameters for Diagnosis of Diseases and Disorders
Cancers of the Reproductive Tract
1. Cervical Cancer:

The Pap-smear is usually evaluated by cytological methods showing normal and cancer cells at different stages of neoplasia routinely classified by the Bethesda system. However, the usefulness of cytological analysis of Pap smear is progressively diminishing; it is replaced by a more cost effective analysis of Human Papilloma virus (HPV) since HPV causes cervical cancer. (Schiffman M, Castle P E, Jeronimo J, Rodriguez A C, Wacholder S. Human papillomavirus and cervical cancer. Lancet 2007; 370(9590):890-907; Centers for Disease Control and Prevention. Division of STD Prevention (1999). *Prevention of genital HPV infection and sequelae: report of an external consultants' meeting.* Atlanta, Ga., 2012; and National Cancer Institute. National Institutes of Health. U.S. Department of Health and Services. HPV and Cancer. world wide web at cancer.gov/cancertopics/factsheet/Risk/HPV#q3; world wide web at cancer.gov/cancertopics/factsheet/detection/Pap-HPV-testing, 2012.) The presence of the virus is a significant diagnostic feature of such cancer. The mechanism is entry and multiplication of the HPV in cervical cells and subsequent transformation of infected cells into neoplasia. An estimate of the level of HPV can be made from PAP smear samples. The level of HPV is an indicator of the risk of cervical cancer. Progression of neoplasia of the cervix is fatal. The absorption capsule of the device is closely opposed to protruded cervical tissue and the capsule of the device collects HPV, cancerous cells and normal cells. There are more than 100 different types of HPV; of which 40 are sexually transmitted and 15 may cause cancer. Among these high risk types are: HPV-16 and HPV-18. The HPV infection is common and often are eliminated naturally. However, persistent infection of HPV may require continued monitoring. According to the methods disclosed herein, cervical cancer is monitored by both cellular analysis and HPV level quantification of biological materials collected by the device which is convenient, painless and noninvasive self-administered in privacy. Analysis of genes associated with the cervical cancer (TROP2, NEDD9, Ki67 [MIB1], Keratin17, OCT4, TMPRSS4, KAP1, ZBRK1, Nestin, ERp57, SOX1) and polymorphisms and variations of genes (EGFR, HLAs, ERBB4, XRCC1) will also improve diagnosis of cervical cancer.

Uterine Cancer:

Multiple diverse genes are involved in different types of uterine cancers. (Garg K, Leitao M Jr, Kauff N, Hansen J, Kosarin K, Shia J, Soslow R. "Selection of endometrial carcinomas for DNA mismatch repair protein immunohistochemistry using patient age and tumor morphology enhances detection of mismatch repair abnormalities" *Am J Surg Pathol.* 2009; 33:925-33; Mutter G L, Lin M, Fitzgerald J, Kum J B, Baak J P, Lees J A, Weng L P, Eng C. "Altered PTEN expression as a diagnostic marker for the earliest endometrial precancers" *J Natl Cancer Inst.* 2000; 92:924-30; Zhang G, Li X, Zhang L, Zhao L, Jiang J, Wang J, Wei L. "The expression and role of hybrid insulin/insulin-like growth factor receptor type 1 in endometrial carcinoma cells" *Cancer Genet Cytogenet.* 2010; 200:140-8; Kim J J, Chapman-Davis E. "Role of progesterone in endometrial cancer" *Semin Reprod Med.* 2010; 28:81-90; Srijaipracharoen S, Tangjitgamol S, Tanvanich S, Manusirivithaya S, et al., "Expression of ER, PR, and Her-2/neu in endometrial cancer: a clinicopathological study" *Asian Pac J Cancer Prev.* 2010; 11:215-20; Konopka B, Janiec-Jankowska A, Czapczak D, Paszko Z, et al., "Molecular genetic defects in endometrial carcinomas: microsatellite instability, PTEN and beta-catenin (CTNNB1) genes mutations" *J Cancer Res Clin Oncol.* 2007; 133:361-71; and Lacey J V Jr, Yang H, Gaudet M M, Dunning A, Lissowska J, et al., "Endometrial cancer and genetic variation in PTEN, PIK3CA, AKT1, MLH1, and MSH2 within a population-based case-control study" *Gynecol Oncol.* 2011; 120:167-73). Uterine cancers are identified using molecular methods (cellular and genomic) and analysis of mutations of genes that promote such cancers. The cells and secretions, and discharged blood, collected by the device, will be analyzed for biomarker proteins (CA-125, HE-4, YKL-40, IL-6, GDF-15 and IGF-1). The deviation in the levels of these biomarkers and genomic changes of these biomarkers are detectable at an early stage of endometrial cancer differentiation. Genes associated with hyperplasia and endometrioid cancers are; PTEN, MLH1, MSH2, 6; PAX2, ESR1, PGR; ETV5/ERM; RUNX1/AML1; PIK3, CTNNB1, CYP19, IGF1R; ARID1A; and those with papillary and serous uterine carcinoma are: TP53, Ki 67, TGF-β1, Nrf2, EGF, HER2/Neu; p16 [CDKN2A], CLDN1, CD151, PTK2, EMP2; EpCAM; IMP3, SSA1, KLK6, VEGF, and WT1. (Kim J J, Chapman-Davis E. "Role of progesterone in endometrial cancer" *Semin Reprod Med.* 2010; 28:81-90; Srijaipracharoen S, Tangjitgamol S, Tanvanich S, Manusirivithaya S, et al., "Expression of ER, PR, and Her-2/neu in endometrial cancer: a clinicopathological study" *Asian Pac J Cancer Prev.* 2010; 11:215-20; Konopka B, Janiec-Jankowska A, Czapczak D, Paszko Z, et al., "Molecular genetic defects in endometrial carcinomas: microsatellite instability, PTEN and beta-catenin (CTNNB1) genes mutations" *J Cancer Res Clin Oncol.* 2007; 133:361-71; and Lacey J V Jr, Yang H, Gaudet M M, Dunning A, Lissowska J, et al., "Endometrial cancer and genetic variation in PTEN, PIK3CA, AKT1, MLH1, and MSH2 within a population-based case-control study" *Gynecol Oncol.* 2011; 120:167-73). These biomarkers and genes will be analyzed by: (i) optical microscopic system for simultaneous visualization and quantitation of multiple biomarker proteins in cell compartments by immunocytochemistry and (ii) next generation gene sequencing system for gene anomalies associated with such cancers collected by the Uterine Device. These data will provide a more accurate diagnosis of the diseases compared to that used presently.

Ovarian Cancer:

Ovarian cancers are derivatives of the embryonic Mullerian duct. The most common sub-type of ovarian cancer, serous ovarian cancer, originates from the fallopian tubes. Serous tubal intraepithelial carcinoma (STICS) cells spread over the ovarian surface and shed into the fallopian tube and peritoneal cavity. These cells may implant in the peritoneum and invade the bowel and bladder. A variety of genes are associated with the ovarian cancers: MUC16, WFDC2, CHI3L1, FOXO3a, HNF-1β, IL6, ARHI (DIRAS3), HMGA2, VGF/PGP9.5, NF-kappaB, HOX, TP53, PR/ER, BRCA-1, -2, TERT, RAD51C and CDKN2A and are used to characterize ovarian cancer sub-types by the genomic assays described. Different protein biomarkers of ovarian cancer (CA 125, HE-4, leptin, IGF II, osteopontin, MIF and others) have been identified and can be quantified in the retrieved biological materials for detection of ovarian cancers. These data generated by the Uterine Device and by a computer program on the Risk of Ovarian Cancer Algorithm (ROCA) primarily based on CA125 levels in patient serum, can predict the risk of developing ovarian cancer potentials and allow an early diagnosis of ovarian cancer.

Genomic Markers for Fetal Birth Defects

Birth Defects Associated with Multiple Genes:

The methods of the invention provide for identification of genomic changes associated with human birth defects. Comprehensive sequencing of the genome may reveal mutations of multiple genes associated with dysmorphogenesis of fetal vital organs and single genes associated with particular functions of a cell. The next generation sequencing system identifies changes in the genome associated with dysmorphogenesis and function of organs. Disorders of interest include but are not limited to the following:

Brain and Neural Tube

Genes Related to Neural Tube Defects (NTDs):

The neural tube closure and neurogenesis represent a major mile stone during in utero fetal development. Neural tube defects are common and debilitating congenital malformations resulted from failure of neural tube closure during early embryonic development. NTDs are produced by anomalies of genes. (De Marco P, Merello E, Cama A, Kibar Z, Capra V. "Human neural tube defects: genetic causes and prevention" Biofactors. 2011 July; 37(4):261-8. doi: 10.1002/biof.170. Epub 2011 Jun. 14; Marini N J, Hoffmann T J, Lammer E J, Hardin J, Lazaruk K, Stein J B, Gilbert D A, Wright C, Lipzen A, Pennacchio L A, Carmichael S L, Witte J S, et al. "A genetic signature of spina bifida risk from pathway-informed comprehensive gene-variant analysis" *PLoS One*. 2011; 6(11):e28408. Epub 2011 November 30; and Obican S G, Funnell R H, Mills J L, Shaw G M, Scialli A R. "Folic acid in early pregnancy: a public health success story" FASEB J. 2010 November; 24(11):4167-74. Epub 2010 Jul. 14). These genes are associated with metabolism of folic acid and supplementation of folic acid to mothers during pregnancy reduces the risk of NTDs by 60-70%. Among the genes for human NTDs, PRICKLE1, FZD6, VANGL1 and 2, and DNA repair MGMT are important. (Bosoi C M, Capra V, Allache R, Trinh V Q, De Marco P, Merello E, Drapeau P, Bassuk A G, Kibar Z. "Identification and characterization of novel rare mutations in the planar cell polarity gene PRICKLE1 in human neural tube defects" *Hum Mutat*. 2011 December; 32 (12):1371-5; De Marco P, Merello E, Rossi A, Piatelli G, Cama A, Kibar Z, Capra V. "FZD6 is a novel gene for human neural tube defects" *Hum Mutat*. 2011 Nov. 1. doi:10.1002/humu.21643; Reynolds A, McDearmid J R, Lachance S, De Marco P, Merello E, Capra V, Gros P, Drapeau P, Kibar Z. "VANGL1 rare variants associated with neural tube defects affect convergent extension in zebrafish" *Mech Dev*. 2010 July-August; 127(7-8):385-92; Kibar Z, Salem S, Bosoi C M, Pauwels E, De Marco P, et al. "Contribution of VANGL2 mutations to isolated neural tube defects" *Clin Genet*. 2011 July; 80(1):76-82. doi:10.1111/j.1399-0004. 2010.01515.x. Epub 2010 Jul. 22; and Tran S, Wang L, Le J, Guan J, Wu L, et al., "Altered Methylation of the DNA Repair Gene MGMT is Associated with Neural Tube Defects" *J Mol Neurosci*. 2011 Nov. 19. [Epub ahead of print]) More than 200 genes may cause NTDs in mice strains, some of the NTDs are not related to folic acid metabolism. (Harris M J. "Insights into prevention of human neural tube defects by folic acid arising from consideration of mouse mutants" *Birth Defects Res A Clin Mol Teratol*. 2009 April; 85(4): 331-9; and Harris M J, Juriloff D M. "An update to the list of mouse mutants with neural tube closure defects and advances toward a complete genetic perspective of neural tube closure" *Birth Defects Res A Clin Mol Teratol*. 2010 August; 88(8):653-69). Comprehensive analysis of genomic changes by the next generation sequencing system will be made with cells and DNAs retrieved by the Uterine Device for assessment of genomic variations associated with the human NTDs.

Holoprocencephaly (HPE):

HPE is a frequent malformation of the forebrain due to incomplete midline cleavage. (Bendavid C, Dupé V, Rochard L, Gicquel I, Dubourg C, David V. Holoprosencephaly: "An update on cytogenetic abnormalities" *Am J Med Genet C Semin Med Genet*. 2010 Feb. 15; 154C(1): 86-92; and Mercier S, Dubourg C, Garcelon N, Campillo-Gimenez B, Gicquel I, et al., "New findings for phenotype-genotype correlations in a large European series of holoprosencephaly cases" *J Med Genet*. 2011 November; 48(11):752-60. Epub 2011 September 22). The molecular basis of such human brain anomalies is unknown. At present, 12 different HPE loci have been identified, and 8 genes seem to be related to HPE. Point mutations of SHH, ZIC2, SIX3 and TGIF genes are found in 20-25% cases. Other anomalies in these genes constitute additional 10%. The ZIC2 mutation affects morphogenesis of the neural tube and neuronal cell migration.

The facial features are related to severity of brain anomalies for patients with SHH, SIX3, and TGIF gene mutations. Microarray analyses revealed that other gene loci and marked chromosomal changes are also associated with HPE. Recently, additional genes: PATCHED1, TDGF1/CRIPTO, FAST1, GLI2 and DHCR have been shown to be involved with HPE. However, early detection by ultrasonographic imaging and comprehensive analysis of gene mutations and genomic changes by next generation sequencing system will profoundly impact their early detection and prevention.

Psychiatric Diseases:

Multiple genes are involved in functional and structural differentiation of neural cells and brain compartments. Among these, neurotrophins play important roles in both normal and disease states. (Zhou Y, Lu T J, Xiong Z Q. "NGF-dependent retrograde signaling: survival versus death" *Cell Res*. 2009 May; 19(5):525-6; Lessmann V, Brigadski T. "Mechanisms, locations, and kinetics of synaptic BDNF secretion: an update" *Neurosci Res*. 2009 September; 65(1):11-22; Lu B, Martinowich K. "Cell biology of BDNF and its relevance to schizophrenia" *Novartis Found Symp*. 2008; 289:119-29; discussion 129-35, 193-5; Bekinschtein P, Cammarota M, Izquierdo I, Medina J H. "BDNF and memory formation and storage" *Neuroscientist*. 2008 April; 14(2):147-56; Chao H M, Kao H T, Porton B. "BDNF Val66Met variant and age of onset in schizophrenia" *Am J Med Genet B Neuropsychiatr Genet*. 2008 Jun. 5; 147B(4):505-6; Fan J, Sklar P. "Genetics of bipolar disorder: focus on BDNF Val66Met polymorphism" *Novartis Found Symp*. 2008; 289:60-72; discussion 72-3, 87-93; Dwivedi Y. "Brain-derived neurotrophic factor: role in depression and suicide" *Neuropsychiatr Dis Treat*. 5:433-49, 2009. Chen L, Lawlor D A, Lewis S J, Yuan W, Abdollahi M R, et al., "Genetic association study of BDNF in depression: finding from two cohort studies and a meta-analysis" *Am J Med Genet B Neuropsychiatr Genet*. 2008 Sep. 5; 147B(6):814-21; Marziniak M, Herzog A, Mössner R, Sommer C. "Investigation of the functional brain-derived neurotrophic factor gene variant Val66MET in migraine" *J Neural Transm.* 2008 September; 115(9): 1321-5; Britsch S. "The neuregulin-I/ErbB signaling system in development and disease" *Adv Anat Embryol Cell Biol.* 190:1-65, 2007; Harrison P J, Law A J. "Neuregulin 1 and schizophrenia: genetics, gene expression, and neurobiology" *Biol Psychiatry.* 60:132-40, 2006; Kéri S, Kiss I, Kelemen O. "Effects of a neuregulin 1 variant on conversion to schizophrenia and schizophreniform disorder in people at high risk for psychosis" *Mol Psychiatry.* 2009 February; 14(2):118-9; Tan W, Wang Y, Gold B, Chen J, Dean M, Harrison P J, Weinberger D R, Law A J. "Molecular cloning of a brain-specific, developmentally regulated neuregulin 1 (NRG1) isoform and identification of a functional promoter variant associated with schizophrenia" *J Biol Chem.* 2007 Aug. 17; 282(33):24343-51; Yang P, Lung F W, Jong Y J, Hsieh H Y, et al., "Association of the homeobox transcription factor gene ENGRAILED 2 with autistic disorder in Chinese children" *Neuropsychobiology.* 57:3-8, 2008; Atz M E, Rollins B, Vawter M P. "NCAM1 association study of bipolar disorder and schizophrenia: polymorphisms and alternatively spliced isoforms lead to similarities and differences" *Psychiatr Genet.* 17:55-67, 2007; Sullivan P F, Keefe R S, Lange L A, Lange E M, Stroup T S, et al., "NCAM1 and neurocognition in schizophrenia" *Biol Psychiatry.* 61:902-10, 2007; Dickinson D, Elvevåg B. "Genes, cognition and brain through a COMT lens" *Neuroscience.* 2009 Nov. 24; 164(1):72-87; and Katerberg H, Cath D C, Denys D A, Heutink P, Polman A, et al. "The role of the COMT Val(158)Met polymorphism in the phenotypic expression of obsessive-compulsive disorder" *Am J Med Genet B Neuropsychiatr Genet.* 2010 Jan. 5; 153B(1):167-76.) Some of these genes are associated with various neurological diseases, such as, schizophrenia, memory loss, psychotic behavior, depression states, and obsessive-compulsive, unipolar-bipolar and autism-spectrum disorders. A comprehensive characterization of the genes: Brian Derive Growth Factor [BDNF], Neuregulin 1 [NRG 1/ErR 4], Engrailed [EN 2, 3]), Neural Cell Adhesion Molecule [N-CAM1], and Catechol-O-methyltransferase [COMT] by next generation genomic analysis in cells and DNA isolated by the Uterine Device during early pregnancy will provide vital information on the origin, intervention and management of these neural diseases later in life.

Heart and Circulatory System

Interactions between multiple genes regulate differentiation and morphogenesis of mammalian heart. (Wolf M, Basson C T. "The molecular genetics of congenital heart disease: a review of recent developments" *Curr Opin Cardiol.* 2010 Feb. 24. [Epub ahead of print]; Butler T L, Esposito G, Blue G M, Cole A D, Costa M W, Waddell L B, et al., "GATA4 mutations in 357 unrelated patients with congenital heart malformation" *Genet Test Mol Biomarkers.* 2010 December; 14(6):797-802; Nadeau M, Georges R O, Laforest B, Yamak A, Lefebvre C, et al. "An endocardial pathway involving Tbx5, Gata4, and Nos3 required for atrial septum formation" *Proc Natl Acad Sci USA.* 2010 Nov. 9; 107(45):19356-61; Stallmeyer B, Fenge H, Nowak-Göttl U, Schulze-Bahr E. "Mutational spectrum in the cardiac transcription factor gene NKX2.5 (CSX) associated with congenital heart disease" *Clin Genet.* 2010 December; 78(6): 533-40; Salazar M, Consoli F, Villegas V, Caicedo V, Maddaloni V, et al., "Search of somatic GATA4 and NKX2.5 gene mutations in sporadic septal heart defects" *Eur J Med Genet.* 2011 May-June; 54(3):306-9; MacGrogan D, Luna-Zurita L, de la Pompa J L. "Notch signaling in cardiac valve development and disease" *Birth Defects Res A Clin Mol Teratol.* 2011 June; 91(6):449-59; Jain R, Rentschler S, Epstein J A. "Notch and cardiac outflow tract development" *Ann N Y Acad Sci.* 2010 February; 1188:184-90; Luna-Zurita L, Prados B, Grego-Bessa J, Luxán G, et al., "Integration of a Notch-dependent mesenchymal gene program and Bmp2-driven cell invasiveness regulates murine cardiac valve formation" *J Clin Invest.* 2010 Oct. 1; 120(10):3493-507; High F A, Jain R, Stoller J Z, Antonucci N B, Lu M M, Loomes K M, et al. "Murine Jagged1/Notch signaling in the second heart field orchestrates Fgf8 expression and tissue-tissue interactions during outflow tract development" *J Clin Invest.* 2009 July; 119 (7):1986-96; and Chen Y H, Ishii M, Sucov H M, Maxson R E Jr. "Msx1 and Msx2 are required for endothelial-mesenchymal transformation of the atrioventricular cushions and patterning of the atrioventricular myocardium" *BMC Dev Biol.* 2008 Jul. 30; 8:75. Many genes involved in development of the heart, for example, GATA 4, NKX2-5, NOTCH1 and TBX-5 have been studied more extensively than others. The roles of the GATA gene (−4, −5 and −6) mutations on congenital malformation of the heart is highly significant. (Butler T L, Esposito G, Blue G M, Cole A D, Costa M W, Waddell L B, et al., "GATA4 mutations in 357 unrelated patients with congenital heart malformation" *Genet Test Mol Biomarkers.* 2010 December; 14(6):797-802). The combination of mutations of GATA-4 and NKX 2.5 genes is associated with sporadic defects of the heart during development. BMPs, FGF8 and Notch family genes, and a number of transcription factors (e.g., Twist1, Tbx18 and 20, Msx1 and Msx2) promote morphogenesis of heart valves. (Chen Y H, Ishii M, Sucov H M, Maxson R E Jr. "Msx1 and Msx2 are required for endothelial-mesenchymal transformation of the atrioventricular cushions and patterning of the atrioventricular myocardium" *BMC Dev Biol.* 2008 Jul. 30; 8:75). The combination of information on gene mutations in the cells collected by the device and in utero imaging by ultrasonography is valuable for prevention and management of such disorders of developing fetus and later in post natal life.

Birth Defects Due to Single Gene Defects:

At present, most frequent mutations of single-gene diseases are screened during in utero fetal development using placental cells obtained by invasive and painful CVS procedure. The next generation sequencing system analysis of cell free DNA and DNA from cells collected by the device will identify multiple mutations and genomic variations and allow for precision diagnosis of a disease or disorder. Application of the next generation sequencing methods, subsequent graphic representation of sequence base changes or other genomic anomalies, and comparison with the existing data bases (National Center for Biotechnology Information, NCBI: GenBank, dbSNP, Unigen, etc.; Catalogue of Somatic Mutations, COSMIC; Online Mendelian Inheritance in Man; OMIM; and others) will allow in-depth analysis of the disorder. A description of such birth defects and the need for comprehensive analysis of genes is given below.

Cystic Fibrosis (CF):

CF is a hereditary disease of transmembrane conductance regulator gene, CFTR, affecting respiratory, pancreatic, liver, digestive and reproductive organs. The gene generates a protein that controls the movement of salt and water in cells, and defects in the gene may produce thick, sticky mucus and salty sweat which are the diagnosis parameters. Approximately, 30,000 individuals in the USA have CF; and 10 million are carriers who can transmit the faulty CFTR gene to their children (world wide web at nhlbi.nih.gov/health/health-topics/topics/cf/names). Defects at multiple sites of the CFTR gene may cause the CF disease. The CF disease has a worldwide distribution with 1903 known mutations of the gene (world wide web at genet.sickkids.on.ca/cftr/Statistics). The most common mutation of the CFTR gene is ΔF508; however, other low frequency mutations may also have a marked functional consequence (world wide web at genet.sickkids.on.ca/cftr/resource).

Muscular Dystrophies (MD):

Muscular Dystrophies are inherited sex-linked lifelong disabilities due weakness or loss of muscle functions of different organs (world wide web at ninds.nih.gov/disorders/md/md.htm). More than 50,000 male are affected in the U.S.A. Mutations and dysfunction of the dystrophin gene (DMD) cause the Duchenne and Becker forms of muscular dystrophy. The DMD gene regulates production of dystrophin protein. This protein is present in skeletal and cardiac muscle stabilizing and protecting muscle fibers. Hundreds of mutations of the dystrophin gene have been identified. The Duchenne form of MD is more common and severe, and the clinical phenotypes are frequently associated with mutations of other genes, POMT1, POMT2, POMGNt1, fukutin and LARGE.

Thalassemia:

Thalassemia is a blood disease caused by β-globin biosynthesis failure with worldwide distribution (world wide web at ncbi.nlm.nih.gov/books/NBK1426/). More than 200 mutations associated with the disease have been identified. The mutation of sites IVSI-1, IVSI-6, IVSI-110 genes and Codon 39 sites are most prevalent and used in the clinical diagnosis of the disease (world wide web at clinchem.org/content).

Tay-Sachs Disease:

It is a fatal disease of ganglioside lipid storage in neural tissues. The incidence is high in some Jewish population (world wide web at ninds.nih.gov/disorders/taysachs). Mutations in the HEXA gene cause Tay-Sachs disease. The HEXA gene regulates beta-hexosaminidase A, which plays a critical role in the brain and spinal cord functions. This enzyme is located in the lysosomes of cells. Mutations in the HEXA gene disrupt the activity of beta-hexosaminidase A preventing the breaking down GM2 ganglioside. As a result, this substance accumulates in neurons in the brain and spinal cord. Progressive buildup of GM2 ganglioside leads to the degeneration of neurons in these organs. There are more than 100 mutations of these genes responsible for the disease. R178H, R499H, W474C, G269S, R505Q, Y277X, C137Y and G353R are common mutations related to Tay-Sachs disease.

Infertility and Window of Embryo Transfer for IVF Procedure

Growth and regulatory factors: LIF, VEGF, TGF-β, Leptin, activin, prolactin, IGFs and IGF-binding proteins, and their receptors, play significant roles in preparation of endometrial tissues for implantation of the embryo. (Hannan N J, Paiva P, Meehan K L, Rombauts L J, et. al., "Analysis of fertility-related soluble mediators in human uterine fluid identifies VEGF as a key regulator of embryo implantation. Endocrinology" 2011 December; 152(12):4948-56; Yang H, Taylor H S, Lei C, Cheng C, Zhang W. "Hormonal regulation of galectin 3 in trophoblasts and its effects on endometrium" *Reprod Sci.* 2011 November; 18(11):1118-27; Kane N M, Jones M, Brosens J J, Kelly R W, et al., *TGFβ1 attenuates expression of prolactin and IGFBP-1 in decidualized endometrial stromal cells by both SMAD-dependent and SMAD-independent pathways. PLoS One.* 2010 Sep. 24; 5(9):e12970; Rocha A L, Carrarelli P, Novembri R, de Pascalis F, et al., "Activin a Stimulates Interleukin 8 and Vascular Endothelial Growth Factor Release From Cultured Human Endometrial Stromal Cells Possible Implications for the Pathogenesis of Endometriosis" *Reprod Sci.* 2012 Apr. 3. [Epub ahead of print]; Zhao H, Jiang Y, Cao Q, Hou Y, Wang C. "Role of Integrin Switch and Transforming Growth Factor Beta 3 in Hypoxia-Induced Invasion Inhibition of Human Extravillous Trophoblast Cells" *Biol Reprod.* 2012 June 6. [Epub ahead of print]; and Li M Q, Luo X Z, Meng Y H, Mei J, Zhu X Y, Jin L P, Li D J. "CXCL8 enhances proliferation and growth and reduces apoptosis in endometrial stromal cells in an autocrine manner via a CXCR1-triggered PTEN/AKT signal pathway" *Hum Reprod.* 2012 July; 27(7):2107-16). Expression of other factors: PIF, EMMPRIN, caspase 1, CD82, PPARγ, Integrins, kissipeptins, corin, and CXCL8 in endometrial and trophoblast cells enhance development and differentiation of embryos and the invasion potential of the trophoblast into the endometrium. Among these factors, Kissipeptins (metastatin) are an important group of factors that influence the implantation of the embryo and irregularities in invasion leading to pregnancy disorders. Similarly, the cytokines are immunoregulatory factors generated by both embryo and endometrial cells. (Boomsma C M, Kavelaars A, Eijkemans M J, Lentjes E G, et al., "Endometrial secretion analysis identifies a cytokine profile predictive of pregnancy in IVF" *Hum Reprod.* 2009 June; 24(6):1427-35; Boomsma C M, Kavelaars A, Eijkemans M J, et al., "Cytokine profiling in endometrial secretions: a non-invasive window on endometrial receptivity" *Reprod Biomed Online.* 2009 January; 18(1):85-94; Rajaei S, Zarnani A H, Jeddi-Tehrani M, et al., "Cytokine profile in the endometrium of normal fertile and women with repeated implantation failure" *Iran J Immunol.* 2011 December; 8(4):201-8; Kalu E, Bhaskaran S, Thum M Y, Vishwanatha R, et al., "Serial estimation of Th1:th2 cytokines profile in women undergoing in-vitro fertilization-embryo transfer" *Am J Reprod Immunol.* 2008 March; 59(3):206-11; Drannik A G, Nag K, Yao X D, Henrick B M, et al., "Trappin-2/elafin modulate innate immune responses of human endometrial epithelial cells to PolyI:C" *PLoS One.* 2012; 7(4):e35866. Epub 2012 Apr. 24; Wallace A E, Fraser R, Cartwright J E. "Extravillous trophoblast and decidual natural killer cells: a remodelling partnership" Hum Reprod Update. 2012 July; 18(4):458-71; and Champion H, Innes B A, Robson S C, Lash G E, Bulmer J N. "Effects of interleukin-6 on extravillous trophoblast invasion in early human pregnancy" *Mol Hum Reprod.* 2012 August; 18(8): 391-400). The interaction of extravillous trophoblast and natural killer cells of decidua may promote endometrial receptivity to embryo implantation. (Drannik A G, Nag K, Yao X D, Henrick B M, et al., "Trappin-2/elafin modulate innate immune responses of human endometrial epithelial cells to PolyI:C" *PLoS One.* 2012; 7(4):e35866. Epub 2012 Apr. 24; Wallace A E, Fraser R, Cartwright J E. "Extravillous trophoblast and decidual natural killer cells: a remodelling partnership" Hum Reprod Update. 2012 July; 18(4):458-71; Champion H, Innes B A, Robson S C, Lash G E, Bulmer J N. "Effects of interleukin-6 on extravillous trophoblast invasion in early human pregnancy" *Mol Hum Reprod.* 2012 August; 18(8):391-400; Chakraborty D, Rumi M A, Konno T, Soares M J. "Natural killer cells direct hemochorial placentation by regulating hypoxia-inducible factor dependent trophoblast lineage decisions" *Proc Natl Acad Sci USA.* 2011 Sep. 27; 108(39):16295-300; Soares M J, Chakraborty D, Renaud S J, Kubota K, et al., "Regulatory pathways controlling the endovascular invasive trophoblast cell lineage" *J Reprod Dev.* 2012; 58(3):283-7; Cai Z, Yang F, Yu L, Yu Z, Jiang L, Wang Q, Yang Y, Wang L, Cao X, Wang J. "Activated T cell exosomes promote tumor invasion via Fas signaling pathway" *J Immunol.* 2012 Jun. 15; 188(12): 5954-61 and Luchetti F, Canonico B, Arcangeletti M, Guescini M, Cesarini E, Stocchi V, Degli Esposti M, Papa S. "Fastsignalling promotes intercellular communication in T cells" *PLoS One.* 2012; 7(4):e35766). In addition, Corticotrophin releasing hormone (CRH) plays a crucial role in implantation of the embryo and the anti-rejection process that protects the fetus from the maternal immune system. (Kalantaridou S N, Zoumakis E, Makrigiannakis A, Godoy H, Chrousos G P. "The role of corticotropin-releasing hormone in blastocyst implantation and early fetal immunotolerance" *Horm Metab Res.* 2007 June; 39(6):474-7).

These factors outlined may modify the endometrium from an immunologically non-privileged site into a privileged site for implantation of the embryo. (Yoshinaga K. "Two concepts on the immunological aspect of blastocyst implantation" *J Reprod Dev.* 2012; 58(2):196-203; Ochiel D O, Ghosh M, Fahey N, Guyre P M, Wira C R. "Human uterine epithelial cell secretions regulate dendritic cell differentiation and responses to TLR ligands" *J Leukoc Biol.* 2010 September; 88(3):435-44; and Makrigiannakis A, Karamouti M, Drakakis P, Loutradis D, Antsaklis A. "Fetomaternal immunotolerance" *Am J Reprod Immunol.* 2008 December; 60(6):482-96). Endometrial tissues undergo cyclical changes in the rate of proliferation, differentiation and apoptosis of cells, associated with the rise and fall in estrogen and progesterone hormones generated by the ovary, and recurring replenishment by the stem cells in uterus. (Li H Y, Chen Y J, Chen S J, Kao C L, Tseng L M, et al., "Induction of insulin-producing cells derived from endometrial mesenchymal stem-like cells" *J Pharmacol Exp Ther.* 2010 December; 335(3):817-29; and Santamaria X, Massasa E E, Feng Y, Wolff E, Taylor H S. "Derivation of insulin producing cells from human endometrial stromal stem cells and use in the treatment of murine diabetes" *Mol Ther.* 2011 November; 19(11):2065-71). The response of endometrial cells to these endocrine, paracrine and autocrine factors on the expression of hormone receptors, different biomarker proteins in cells of the endometrium, and receptivity for embryo implantation, will be reflected in the cells and secretions retrieved by the device. The deviations in the levels of expression of various cytokines, endometrial proteins, and genomic changes in the biological materials collected by the device are also important, and may indicate infertility status. (Renner S P, Strick R, Oppelt P, Fasching P A, Engel S, et al., "Evaluation of clinical parameters and estrogen receptor alpha gene polymorphisms for patients with endometriosis" *Reproduction.* 2006 January; 131(1): 153-61; Kyurkchiev D S, Ivanova-Todorova E, Kyurkchiev S D. "Effect of progesterone on human mesenchymal stem cells" *Vitam Horm.* 2011; 87:217-37; and Lam E W, Shah K, Brosens J J. "The diversity of sex steroid action: the role of micro-RNAs and FOXO transcription factors in cycling endometrium and cancer" *Endocrinol.* 2012 January; 212 (1): 13-25).

Sexually Transmitted Diseases

The major STDs in the USA, besides HIV and HPV, are genital herpes complex virus 2, chlamydia, gonorrhea and syphilis. The uterine microbiome of diverse microbes populating the lower genital tract is monitored frequently by the device, and the microbes analyzed by molecular methods. (Lamont R F, Sobel J D, Akins R A, Hassan S S, et al., "The vaginal microbiome: new information about genital tract flora using molecular based techniques" *BJOG.* 2011 April; 118(5):533-49; Brotman R M. "Vaginal microbiome and sexually transmitted infections: an epidemiologic perspective" *J Clin Invest.* 2011 December; 121(12):4610-7; Hammerschlag M R, Gaydos C A. "Guidelines for the use of molecular biological methods to detect sexually transmitted pathogens in cases of suspected sexual abuse in children" *Methods Mol Biol.* 2012; 903:307-17; Huang C T, Li S Y. "Protocol for the Use of a Bead Array for the Multiple Detection of Genotype of Chlamydia trachomatis" *Methods Mol Biol.* 2012; 903:195-204; Stevens M P, Twin J, Fairley C K, Donovan B, Tan S E, et al., "Development and evaluation of an ompA quantitative real-time PCR assay for Chlamydia trachomatis serovar determination" *J Clin Microbiol.* 2010 June; 48(6):2060-5. Epub 2010 Apr. 14; Tang J, Bansal A. "Protocol for analyzing human leukocyte antigen variants and sexually transmitted infections: from genotyping to immunoassays" *Methods Mol Biol.* 2012; 903:359-80; and Hegazy M M, El-Tantawy N L, Soliman M M, El-Sadeek E S, El-Nagar H S. "Performance of rapid immunochromatographic assay in the diagnosis of Trichomoniasis vaginalis" *Diagn Microbiol Infect Dis.* 2012 June 21. [Epub ahead of print]) Comprehensive immunological assays and genotyping may identify variant microbes and mutations associated with the drug resistant variety. Computational software improves the diagnosis process, infection incidences, workflows, and clinical decisions. (Coveney P V, Shublaq N W. "Computational biomedicine: a challenge for the twenty-first century" *Stud Health Technol Inform.* 2012; 174:105-10; and Carlin E, Taha Y. "Using recent infection testing algorithm tests in clinical practice" *Sex Transm Infect.* 2012 June; 88(4):304-6).

Infection of herpes virus produces common broad spectrum diseases, and such infection may enhance the susceptibility of a subject to other STDs, including HIV. Close monitoring is required during pregnancy as such viral infections significantly increase the rates of preterm delivery, premature rupture of chorionic membranes, preterm labor, intrauterine fetal growth restriction (IUGR), and spontaneous abortion. (Van Wagoner N J, Hook E W 3rd. "Herpes diagnostic tests and their use" *Curr Infect Dis Rep.* 2012 April; 14(2):175-84; Kim I D, Chang H S, Hwang K J. "Herpes simplex virus 2 infection rate and necessity of screening during pregnancy: a clinical and seroepidemiologic study" *Yonsei Med J.* 2012; 53(2):401-7; and Straface G, Selmin A, Zanardo V, De Santis M, Ercoli A, Scambia G. "Herpes simplex virus infection in pregnancy" *Infect Dis Obstet Gynecol.* 2012; 2012:385697; Epub 2012 Apr. 11). Chlamydia infection causes at least urethritis, cervicitis and the sequelae of pelvic inflammatory disease (PID), chronic pelvic pain, ectopic pregnancy and tubal factor infertility. (Mitka M. "CDC: improve targeted screening for chlamydia" *JAMA.* 2012 Apr. 11; 307(14):1472; Gottlieb S L, Berman S M, Low N. "Screening and treatment to prevent sequelae in women with Chlamydia trachomatis genital infection: how much do we know?" *J Infect Dis.* 2010 Jun. 15; 201 Suppl 2:S156-67; Haggerty C L, Gottlieb S L, Taylor B D, et al., "Risk of sequelae after Chlamydia trachomatis genital infection in women" *Infect Dis.* 2010 Jun. 15; 201 Suppl 2:S134-55; Molano M, Meijer C J, Morré S A, Pol R, van den Brule A J. "Combination of PCR targeting the VD2 of omp1 and reverse line blot analysis for typing of urogenital Chlamydia trachomatis serovars in cervical scrape specimens" *J Clin Microbiol.* 2004 July; 42(7):2935-9; and Byrne G I. "Chlamydia trachomatis strains and virulence: rethinking links to infection prevalence and disease severity" *J Infect Dis.* 2010 Jun. 15; 201 Suppl 2:S126-33). Incidences of STDs among teen and young adults of 15-25 years are high and responsible for approximately 18% infertility cases. Chlamydia infection is most prevalent, diagnosed by RFLP genotyping and sequence features of 9 polymorphic outer membrane genes (omp) in cervical scrape samples. The type of membrane proteins, virulence factors (e.g., type III cytotoxins), and stress response proteins are parameters for screening for strains of chlamydia.

Gonorrhea is caused by infection of mucous membrane of reproductive tracts by *Neisseria gonorrhoeae*. The clinical symptoms in women are: dysuria, vagina discharge or bleeding. Infection can spread into the uterus and fallopian tubes and may cause pelvic inflammatory disease (PID) causing infertility and ectopic pregnancy. The risk to the neonate of birth defects (e.g., blindness and joint infection). Resistance of these microbes to treatments is a major global concern; polymorphism of penA, mtrR, proB1b, and ponA genes is associated with such resistance. (Unemo M, Dillon J A. "Review and international recommendation of methods for typing *neisseria gonorrhoeae* isolates and their implications for improved knowledge of gonococcal epidemiology, treatment, and biology" *Clin Microbiol Rev.* 2011 July; 24(3):447-58; Martin I, Sawatzky P, Allen V, Hoang L, et al., "Emergence and characterization of *Neisseria gonorrhoeae* isolates with decreased susceptibilities to ceftriaxone and cefixime in Canada: 2001-2010" *Sex Transm Dis.* 2012 April; 39(4):316-23; Lindberg R, Fredlund H, Nicholas R, Unemo M. "*Neisseria gonorrhoeae* isolates with reduced susceptibility to cefixime and ceftriaxone: association with genetic polymorphisms in penA, mtrR, porB1b, and ponA" *Antimicrob Agents Chemother.* 2007 June; 51(6):2117-22; Whiley D M, Goire N, Ray E S, Limnios A, Lambert S B, et al., "*Neisseria gonorrhoeae* multi-antigen sequence typing using non-cultured clinical specimens" *Sex Transm Infect.* 2010 February; 86 (1):51-5; and Liao M, Helgeson S, Gu W M, Yang Y, Jolly A M, Dillon J A. "Comparison of *Neisseria gonorrhoeae* multiantigen sequence typing and porB sequence analysis for identification of clusters of *N. gonorrhoeae* isolates" *J Clin Microbiol.* 2009 February; 47(2):489-91).

Syphilis is caused by the bacterium, *Treponema pallidum*, with transmission via sexual contacts (world wide web at cdc.gov/mmwr/preview/mmwrhtml/mm5914a1.htm). In pregnant women with active syphilis disease, there is a 50% risk of early fetal loss, stillbirth, and delivery of neonates with low birth weight and congenital defects of deafness, neurologic impairment, and bone deformities. The impacts of such congenital syphilis (CS) disorders are severe on the postnatal and adult life. Women with primary syphilis often are asymptomatic. Collection of samples of microbes from the direct source is superior for diagnosis of the disease by molecular tests. (De Santis M, De Luca C, Mappa I, Spagnuolo T, et al., "Syphilis Infection during Pregnancy: Fetal Risks and Clinical Management" *Infect Dis Obstet Gynecol.* 2012; 2012:430585. Epub 2012 Jul. 4; Ho E L, Lukehart S A. "Syphilis: using modern approaches to understand an old disease" *J Clin Invest.* 2011 December; 121(12):4584-92; Smajs D, Norris S J, Weinstock G M. "Genetic diversity in *Treponema pallidum*: implications for pathogenesis, evolution and molecular diagnostics of syphilis and yaws" *Infect Genet Evol.* 2012 March; 12(2):191-202; Mikalová L, Strouhal M, Čejková D, Zobaníková M et al., "Genome analysis of *Treponema pallidum* subsp. *pallidum* and subsp. *pertenue* strains: most of the genetic differences are localized in six regions" *PLoS One.* 2010 Dec. 29; 5(12):e15713; and Peng R R, Wang A L, Li J, Tucker J D, Yin Y P, Chen X S. "Molecular typing of *Treponema pallidum*: a systematic review and meta-analysis" *PLoS Negl Trop Dis.* 2011 November; 5(11):e1273. doi: 10.1371/journal.pntd.0001273). The Uterine Device may collect samples directly from the developing conceptus. The CS may be prevented by early diagnosis and subsequent treatment.

Application of these devices and methods of the present invention for early diagnosis of diseases and disorders of women, such as, cancers of reproductive organs, disorders of pregnancy, fetal birth defects, and microbial infections, will markedly change the paradigm of reproductive health care of women, in part because they allow for frequent and convenient monitoring. Early diagnosis of these diseases and disorders will permit early intervention which will reduce medical care costs and improve the quality of life.

EXAMPLES

Example 1

Collection of Biological Samples

The biological materials are retrieved from adult women of reproductive age (20-35 years), perimenopausal and menopausal (45-60 years). In addition, such biological materials are from women undergoing hysterectomy and with cancers of the reproductive organs, in particular, uterine cancer, diagnosed by conventional methods and exposure to risk factors. The biological materials of the platform are examined for cancer biomarkers and specific cells are cultured in a 3-D culture system or frozen (−156° C.) for future analysis. The lesion exudates and spotted blood from the subject are of interest since 6% of women with vaginal bleeding have endometrial cancers.

Example 2

Assay of Uterine Cancer Biomarkers

The biomarkers specific for various types of cancers are assayed by ELISA in the extracts of the platform, blood sera of the subjects and uterine washes. The biomarkers for endometriod cancers are: CA125 (MUC16; cell surface mucin), HE4 (WFDC2; disulfide secretory protease inhibitor), and YKL40 (CHI3L1; chitinase 3-like cartilage protein), and the biomarkers for some serous carcinoma are: IL6 [interferon $\beta_2$], GDF-15 [bone morphogenetic protein], and IGF1 [somatomedin C]. These biomarkers are assayed for in the above samples. Significant differences between the groups are assessed using ANOVA. Relationships of neoplasia or other conditions identified by pelvic examination and biomarkers levels are evaluated by Linear and Logistic Regression Analyses.

Pre-cancer and cancer cells and macromolecules in retrieved biological materials from normal subjects and those with uterine cancers are analyzed for expression of genes in cells by multispectral immunocytochemistry and anomalies of genes by next generation gene sequencing systems.

Example 3

Purification and 3-D Culture of Pre-Cancer and Cancer Cells

Cells of the uterine device of the invention are separated by centrifugation, and specific cells isolated by Magnetic Cell Sorting using antibody and Laser Tweezers. The isolated pre-cancer and cancer cells, control cell lines (Ishikawa, Hec1A, HES) and biopsy samples of the uterus are cultured over biodegradable scaffolds (Cytodex-3, honeycomb PGA and PLA biopolymer) in culture media with sera in rotating reactors of a 3-D culture system (Synthecon, Inc.; see the world wide web at synthecon.com). Such a culture system allows differentiation of cells and tissue formation which resemble that which occurs in vivo.

Example 4

Microscopic Analysis

Neoplastic cells express multiple factors simultaneously which presumably interact to induce the development of specific types of cancer cells. Therefore, simultaneous analysis of multiple parameters in cells and 3-D imaging of cells facilitates identification of the pathology. A highly sensitive multispectral optical system for simultaneous localization of multiple cell parameters by immunocytochemistry is used. This system is used for analysis of such molecular parameter expression in retrieved cells.

Example 5

Genomic Alteration Analysis

The next-generation gene sequencing systems permit rapid sequencing and accurate identification of anomalies of genes specific to various diseases. Such gene (DNA) sequencing systems from the Illumina, Inc. are efficient and accurate (world wide web at illumina.com/technology/sequencing; MiSeq system). This system uses "sequencing by synthesis technology" as a sequencing platform allowing for parallel and rapid sequencing of DNA to identify base variations, mutations and other gene anomalies. The Nextera DNA preparation kits are used for extraction and preparation of DNA for gene sequencing (world wide web at illumina.com/technology/sequencing).

Various embodiments of the present invention may be characterized by the claims provided at the end of this application.

The embodiments of the invention described above are intended to be merely exemplary; numerous variations and modifications will be apparent to those skilled in the art. All such variations and modifications are intended to be within the scope of the present invention as defined in any appended claims.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A device for retrieving biological materials of the uterus and/or cervix of a subject comprising:
  a receptacle having an open end configured to be placed over the cervix and a wall defining a variable volume receptacle cavity;
  wherein the device further comprises a flexible pouch and a controller, wherein expansion or compression of the pouch generates suction inside the cavity; and wherein the controller is configured to change the volume of the receptacle cavity by expanding or compressing the pouch;

the controller having a proximal end and a distal end.

2. The device according to claim 1, further comprising:
a removable surface for collection of the biological materials, the surface having an anterior wall facing the open end of the receptacle and a posterior wall facing opposite to the open end of the receptacle; and
wherein the pouch is hollow inside and having a second anterior wall facing the open end of the receptacle and a second posterior wall facing opposite of the open end of the receptacle wall; wherein the surface is removably fitted within the receptacle cavity.

3. The device according to claim 1, wherein the receptacle further comprises a flexible rim extending from the open end and attaching the receptacle over the cervix.

4. The device according to claim 1, wherein the receptacle is made of silicone or a synthetic polymer.

5. The device according to claim 1, wherein the surface further comprises:
a pull tab for detaching the surface from the receptacle cavity; and
a platform holding a matrix or mesh of permeable substrate materials.

6. The device according to claim 5, wherein the substrate materials are selected from the group consisting of: cotton mesh, nylon mesh, collagen matrix, hydrogel matrix, synthetic sponge or tissue culture scaffold.

7. The device according to claim 2, wherein the pouch is an inflated pouch.

8. The device according to claim 7, the inflated pouch comprising one or more perforations on the second posterior wall.

9. The device according to claim 8, wherein the controller is configured to expel air contained in the pouch through the perforations of the posterior wall to generate suction.

10. The device according to claim 2, wherein the pouch is a compressed pouch.

11. The device according to claim 10, the compressed pouch comprising one or more pillars separating the second anterior wall and the second posterior wall.

12. The device according to claim 1, wherein the proximal end comprises a handle and the distal end comprises a bead.

13. The device according to claim 4, wherein the silicone is medical grade.

14. The device according to claim 1, further comprising:
a removable surface; and
a flexible pouch; wherein the surface is removably fitted within the receptacle cavity.

15. The device according to claim 1, wherein the receptacle further comprises a flexible rim extending from the open end.

16. The device according to claim 5, wherein the matrix or mesh contains a solution for irrigation and washing of the cervix.

17. The device according to claim 16, wherein the solution is physiological saline or tissue culture media.

18. The device according to claim 16, wherein the irrigation solution comprises a proteolytic enzyme, collagenase, and or DNase.

19. The device according to claim 18, wherein the proteolytic enzyme comprises trypsin, pronase and or proteinase K.

20. A method of retrieving biological materials of the uterus and/or cervix of a subject comprising the steps of:
providing a device having a receptacle with an open end and a wall defining a variable volume receptacle cavity, wherein the device further comprises a flexible pouch, wherein expansion or compression of the pouch generates suction inside the cavity; and wherein the device further comprises a controller configured to change the volume of the receptacle cavity by expanding or compressing the pouch;
positioning the open end of the device facing the cervix of the subject;
generating suction by changing the volume of the pouch cavity through the controller;
collecting biological material from the uterus and/or cervix of the subject; and
removing the device after a specified time period.

21. The method according to claim 20, further comprising the step of:
analyzing the biological material to identify a subject with a particular disease or disorder.

22. The method according to claim 20, wherein the biological material collected is selected from the group consisting of: uterine cells, cervical cells, glandular secretions, migrating WBCs, migrating RBCs, placental cells, fetal cells, peritoneal fluid of the abdomen, DNA, RNA, antibodies and pathologic microbes.

23. The method according to claim 20, wherein the disease or disorder is selected from the group consisting of uterine cancer, cervical cancer, ovarian cancer, a disorder of pregnancy, a developmental defect, infertility, and microbial infection.

* * * * *